(12) United States Patent
Dam

(10) Patent No.: US 8,770,881 B2
(45) Date of Patent: Jul. 8, 2014

(54) SANITIZATION APPARATUSES, KITS, AND METHODS

(75) Inventor: Tuan Dam, Round Rock, TX (US)

(73) Assignee: Cleanint LLC, Georgetown, TX (US)

(*) Notice: Subject to any disclaimer, the term of this patent is extended or adjusted under 35 U.S.C. 154(b) by 768 days.

(21) Appl. No.: 12/820,876

(22) Filed: Jun. 22, 2010

(65) Prior Publication Data

US 2010/0322699 A1    Dec. 23, 2010

Related U.S. Application Data

(60) Provisional application No. 61/219,634, filed on Jun. 23, 2009.

(51) Int. Cl.
*A46B 11/00* (2006.01)

(52) U.S. Cl.
USPC ............................................. 401/11; 401/10

(58) Field of Classification Search
USPC ................ 401/9–11, 196; 15/104.92, 104.93
See application file for complete search history.

(56) References Cited

U.S. PATENT DOCUMENTS

| | | | | |
|---|---|---|---|---|
| 2,255,154 A | * | 9/1941 | Esposito | 15/256.6 |
| 4,821,748 A | * | 4/1989 | Reas | 131/329 |
| 5,683,655 A | | 11/1997 | Carter | 422/28 |
| 5,722,537 A | | 3/1998 | Sigler | 206/205 |
| 6,256,388 B1 | | 7/2001 | Morrow | 379/452 |
| 6,796,314 B1 | | 9/2004 | Graff | 134/1.2 |
| 7,511,283 B2 | | 3/2009 | Chor | 250/455.11 |
| 7,518,047 B2 | | 4/2009 | Koszela | 84/287 |
| 2003/0172545 A1 | | 9/2003 | Vitantonio et al. | 34/266 |
| 2006/0076743 A1 | | 4/2006 | Dunser | 280/33.992 |
| 2006/0267299 A1 | | 11/2006 | Dunser | 280/33.992 |
| 2007/0189643 A1 | | 8/2007 | Tresenfeld | 383/105 |
| 2007/0207073 A1 | | 9/2007 | Drucker | 422/292 |
| 2008/0067419 A1 | | 3/2008 | Shih | 250/455.11 |
| 2008/0265179 A1 | | 10/2008 | Havens et al. | 250/492.1 |

FOREIGN PATENT DOCUMENTS

| | | |
|---|---|---|
| GB | 2 417 887 | 3/2006 |
| GB | 2 446 054 | 7/2008 |

OTHER PUBLICATIONS

International Search Report of PCT Application PCT/US2010/039459, dated Mar. 29, 2011.

* cited by examiner

*Primary Examiner* — David Walczak

(74) *Attorney, Agent, or Firm* — Fulbright & Jaworski, LLP

(57) ABSTRACT

Sanitization apparatuses, kits, and methods, such as, for example, for pens, styluses, handles, remote controls, and pagers.

15 Claims, 18 Drawing Sheets

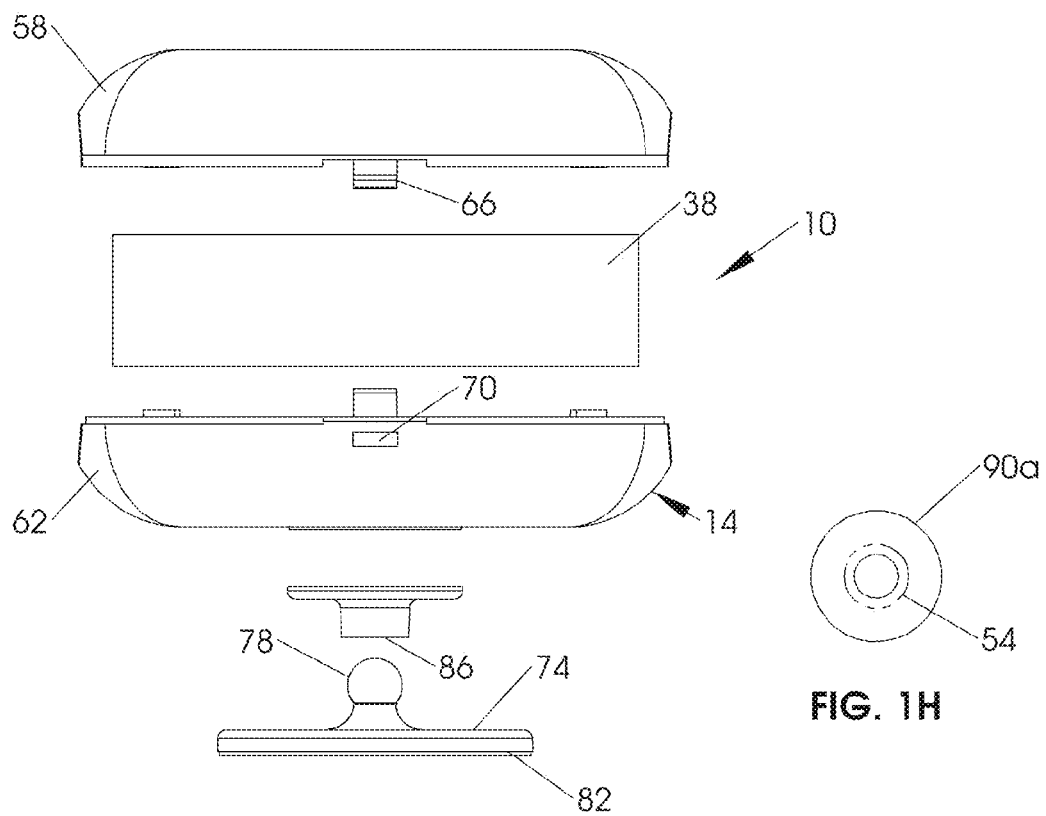
FIG. 1G
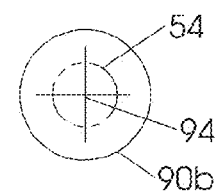
FIG. 1H
FIG. 1J
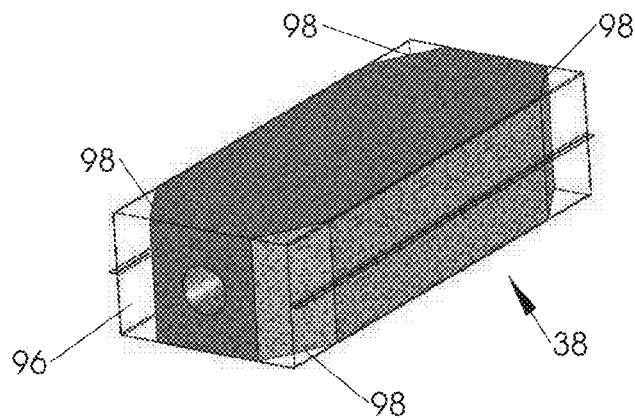
FIG. 2

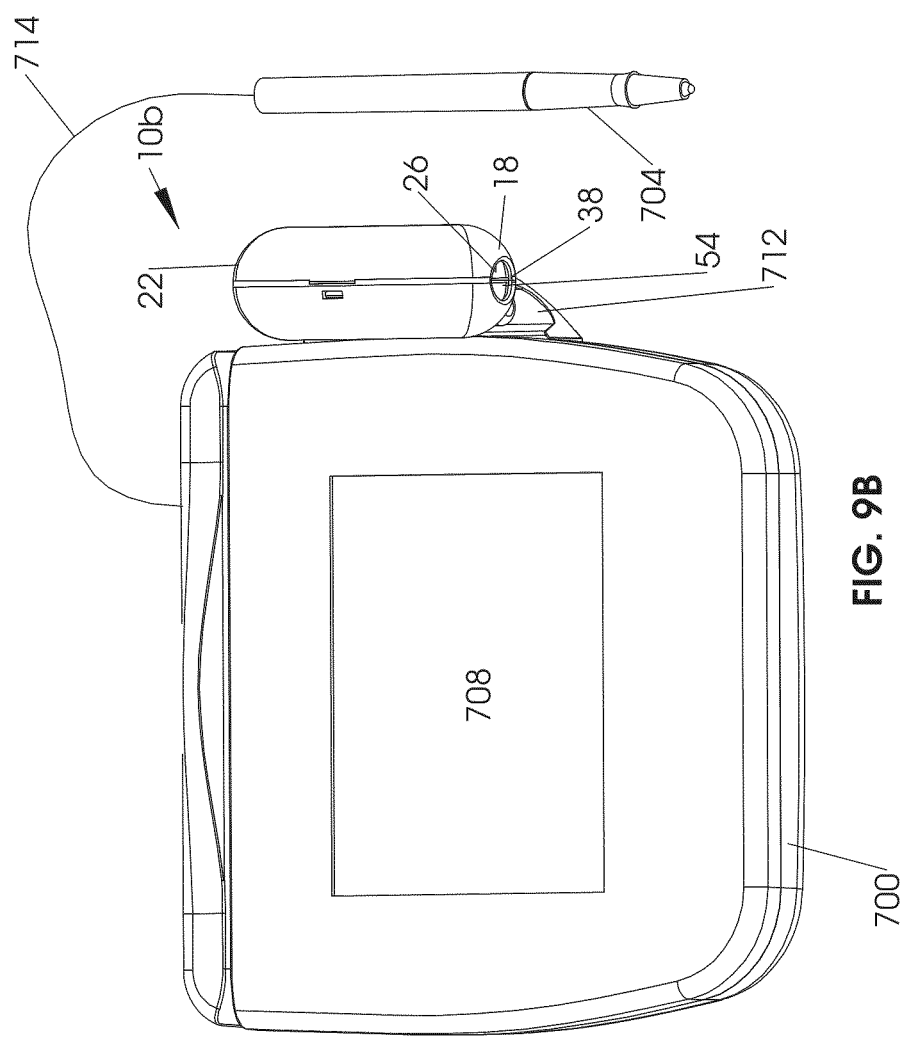

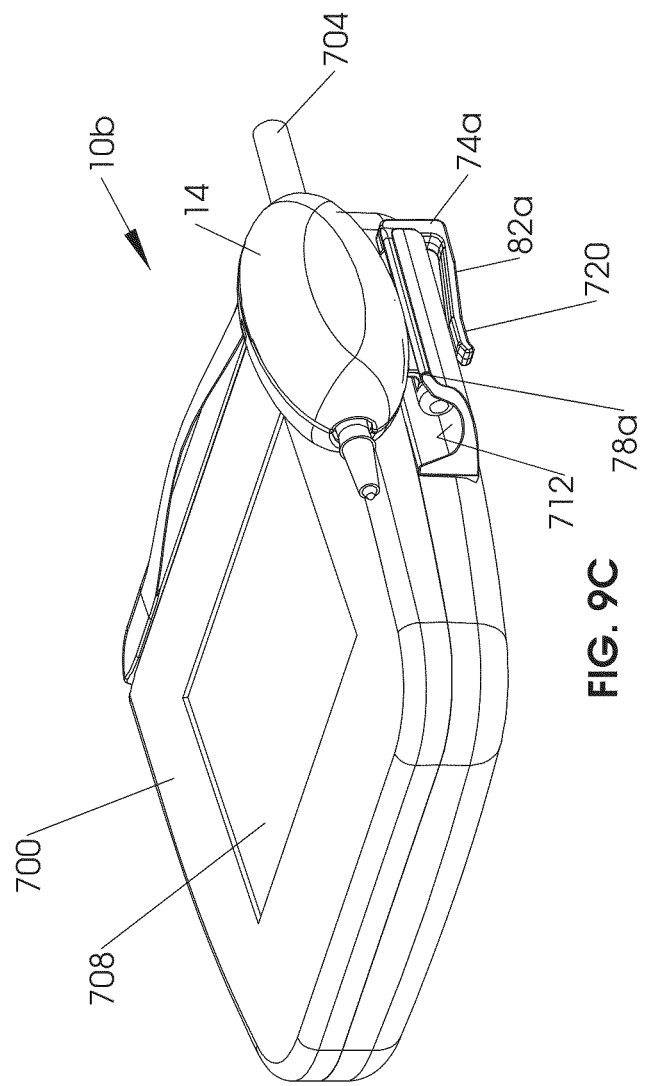

SANITIZATION APPARATUSES, KITS, AND METHODS

RELATED APPLICATIONS

This application claims the benefit of U.S. Provisional Patent Application No. 61/219,634, filed Jun. 23, 2009, which is incorporated by reference in its entirety.

BACKGROUND

1. Field of the Invention

The present invention relates generally to sanitization, and, more particularly, but not by way of limitation, to apparatuses, kits, and methods for sanitization of various objects.

2. Description of Related Art

A number of devices and methods for sanitizing objects are known in the art. Bacteria, germs, viruses, and the like can be harmful and/or dangerous (e.g., may transmit colds, the flu, and/or other illnesses). While hand sanitizing gels are known in the art, even if used frequently, they may be relatively ineffective since even recently sanitized hands often grasp objects that have not been sanitized.

SUMMARY

The present disclosure includes various embodiments of apparatuses, kits, and methods for sanitizing (e.g., disinfecting) various objects, such as, for example, pens (e.g., pens, pencils, styluses for credit card machines, etc.), remote controls (e.g., in hotels or other public places), pagers (e.g., restaurant pagers), shopping cart handles (e.g. in grocery stores), etc.

Some embodiments of the present pen-sanitization apparatuses comprise: a housing having a first end and a second end, the housing defining a first opening through the first end, a second opening through the second end, and a chamber in fluid communication with the first and second openings, the housing configured to open to permit a user to access the chamber; and a fluid-permeable sponge applicator having a first end, a second end, and a length extending between the first and second ends, the sponge applicator defining a passage extending through the sponge applicator and through the first and second ends of the sponge applicator, the passage having a substantially circular cross-section; where the housing is configured to removably receive the sponge applicator in the chamber (e.g., when the housing is closed) such that the passage is substantially aligned with the first and second openings of the housing so that a pen can be passed sequentially through the first opening, the passage, and the second opening such that when passed through the passage the sponge applicator contacts more than half of the cross-sectional perimeter of the pen.

In some embodiments, the passage has a relaxed inner diameter of between (e.g., about) 0.1 and 0.5 inches. In some embodiments, the passage has a relaxed inner diameter of between (e.g., about) 0.2 and 0.4 inches. In some embodiments, the sponge applicator encircles the entire length of the passage, and where the apparatus is configured such that pens having various diameters within a functional range can be passed sequentially through the first opening, passage, and second opening such that when passed through the passage the sponge applicator contacts more than half of the cross-sectional perimeter of the pen. In some embodiments, the functional range is between (e.g., about) 0.2 inches and 0.4 inches. In some embodiments, the apparatus is configured such that pens having various diameters within a functional range can be passed sequentially through the first opening, passage, and second opening such that when passed through the passage the sponge applicator contacts the entire cross-sectional perimeter of at least a portion of the pen. In some embodiments, the first and second ends of the sponge applicator are configured to be fluid-impermeable. In some embodiments, the first and second ends of the sponge applicator are coated with a fluid-impermeable material. In some embodiments, an outer surface (e.g., all of an outer surface) of the sponge applicator between the first and second ends of the sponge applicator are coated with a fluid impermeable material.

Some embodiments further comprise: two end members each coupled to the housing adjacent a different one of the first and second openings of the housing such that the end member covers a portion of the coupled opening. In some embodiments, the end members are each resilient and configured such that if a pen is passed through the respective one of the first and second openings of the housing, the end member will deform to permit the pen to pass through the opening such that the pen contacts the end member as the pen passes through the opening. In some embodiments, the end members are each configured to substantially cover the respective one of the first and second openings when a pen is not passed through the respective opening. In some embodiments, the end members each comprise a resilient flap having one or more slits defining a plurality of subflaps and configured such that if a pen is passed through the respective opening of the housing, the subflaps will move apart as the pen passes through the end member and will move together when the pen is removed from the end member.

In some embodiments, the housing is configured to be removably coupled to a mount. In some embodiments, the housing comprise a first housing member and a second housing member, and is configured to be opened by separating a portion of the first housing member from a portion of the second housing member, and is configured to be removably coupled to a mount by disposing a portion of the mount between the first and second housing members and closing the housing. In some embodiments, at least one of the first housing member and the second housing member defines a notch such that the housing is configured to receive a portion of the mount between the first housing member and the second housing member such that the mount is substantially prevented from being removed from the housing unless the housing is at least partially opened. In some embodiments, the mount includes at least one of: a stand configured to support the apparatus relative to a surface, a stand configured to be coupled to a point-of-sale device, or a lanyard. Some embodiments comprise the mount.

Some embodiments further comprise: a stand having a first end configured to be coupled to the housing and a second end configured to be coupled to a surface such that the stand supports the apparatus. In some embodiments, the second end of the stand comprises an adhesive. In some embodiments, the second end of the stand comprises a suction cup. In some embodiments, the first end of the stand is configured to be pivotally coupled to the housing.

In some embodiments, the housing includes one or more lanyard loops external to the chamber, the one or more lanyard loops configured to receive a lanyard. Some embodiments further comprise: a lanyard configured to be coupled to the one or more loops.

In some embodiments, the housing comprises a first housing member and a second housing member, and where the housing is configured to open by separating a portion of the first housing member from a portion of the second housing member. In some embodiments, the first housing member is pivotally coupled to the second housing member. In some embodiments, where the second housing member is configured to be coupled to the first housing member to define the chamber and configured to be separated from the first housing member to permit a user to access the chamber.

Some embodiments further comprise: a liquid crystal display (LCD) screen. In some embodiments, the LCD screen is configured to display the time.

Some embodiments further comprise: a sanitization fluid absorbed in the sponge applicator. In some embodiments, the sanitization fluid is a liquid. In some embodiments, the sanitization fluid is a gel. In some embodiments, the sanitization fluid comprises one or more ingredients selected from the group consisting of: alcohols, ethanol, isopropanol, aldehydes, oxidizing agents, acids, phenolics, ammoniums, and chlorine.

In some embodiments, the apparatus is configured such that if the sponge applicator is disposed in the chamber and a pen is passed sequentially through the first opening, the passage, and the second opening, the sanitization fluid is applied to the pen by the sponge applicator without any external pumping mechanism. In some embodiments, the first and second openings of the housing are each circular and have a diameter that is larger than the relaxed inner diameter of the passage through the sponge applicator.

Some embodiments of the present methods comprise: providing a pen sanitization apparatus that comprises a housing, a sponge applicator, and a sanitization fluid absorbed in the sponge applicator; and passing a pen through the passage of the sponge applicator such that a portion of the sanitization fluid is disposed on the pen.

Some embodiments of the present sanitization kits comprise: a housing having a first end and a second end, the housing defining a first opening through the first end, a second opening through the second end, and a chamber in fluid communication with the first and second openings, the housing configured to open to permit a user to access the chamber; and two or more fluid-permeable sponge applicator having a first end, a second end, and a length extending between the first and second ends, the sponge applicator defining a passage extending through the sponge applicator and through the first and second ends of the sponge applicator; where the housing is configured to removably receive the sponge applicator in the chamber (e.g., when the housing is closed) such that the passage is substantially aligned with the first and second openings of the housing so that a pen can be passed sequentially through the first opening, the passage, and the second opening such that when passed through the passage the sponge applicator contacts more than half of the cross-sectional perimeter of the pen; and where the housing is configured to removably and interchangeably receive each of the two or more sponge applicators individually.

Some embodiments of the present pen-sanitization apparatuses comprise: a housing having body with a first end and a second end, the housing defining a first opening through the first end, and an elongated tubular portion extending from the second end of the body, the body defining a chamber in fluid communication with the first and opening and the tubular portion, the housing configured to open to permit a user to access the chamber; and a fluid-permeable sponge applicator having a first end, a second end, and a length extending between the first and second ends, the sponge applicator defining a passage extending through the sponge applicator and through the first and second ends of the sponge applicator, the passage having a substantially circular cross-section; where the housing is configured to removably receive the sponge applicator in the chamber such that the passage is substantially aligned with the first opening and the tubular portion of the housing so that a portion of a pen can be passed sequentially through the first opening and the passage, and into the tubular portion such that when passed through the passage the sponge applicator contacts more than half of the cross-sectional perimeter of the pen. In some embodiments, the apparatus is configured such that if a pen is disposed in the housing with a portion of the pen extending into the tubular portion, at least one of the sponge applicator and the tubular portion of the housing will resist removal of the pen from the housing.

Some embodiments of the present handle-sanitization apparatuses comprise: a housing having a first end and a second end, the housing defining a first opening through the first end, a second opening through the second end, and a chamber in fluid communication with the first and second openings; and a fluid-permeable sponge applicator having a first end, a second end, and a length extending between the first and second ends, the sponge applicator defining a passage extending through the sponge applicator and through the first and second ends of the sponge applicator, the passage having a substantially circular cross-section defined by a relaxed inner diameter; where the first and second openings of the housing each have a minimum inner dimension that is larger than the relaxed inner diameter of the passage through the sponge applicator; and where the apparatus is configured to be removably coupled to a handle such that the handle extends through the first opening, the passage, and the second opening and the sponge applicator contacts more than half of the cross-sectional perimeter of the handle.

In some embodiments, the housing has a first housing member and a second housing member configured to be coupled to the first housing member to define the chamber and configured to be separated from the first housing member to permit a user to access the chamber. In some embodiments, the passage has a relaxed inner diameter of between (e.g., about) 1.0 and 2.0 inches. In some embodiments, the passage has a relaxed inner diameter of between (e.g., about) 1.3 and 1.7 inches. In some embodiments, the passage has a relaxed inner diameter of (e.g., about) 1.5 inches.

In some embodiments, the minimum inner dimension of each of the first and second openings is between (e.g., about) five and fifty percent larger than the relaxed inner diameter of the passage. In some embodiments, the minimum inner dimension of each of the first and second openings is between (e.g., about) twenty and thirty percent larger than the relaxed inner diameter of the passage. In some embodiments, the minimum inner dimension of each of the first and second openings is at least ten percent larger than the relaxed inner diameter of the passage.

In some embodiments, the housing is configured to be removably coupled to a handle such that the sponge applicator contacts the entire cross-sectional perimeter of at least a portion of the handle. In some embodiments, the sponge applicator comprises a slit extending between the first and second ends of the sponge applicator such that the sponge applicator can be wrapped around a handle such that the handle is disposed in the passage. In some embodiments, the housing comprises one or more recesses each configured to receive an insert and where the apparatus comprises one or more transparent covers each configured to be removably coupled to the housing such that the cover substantially encloses the recess and will retain an insert in the recess. In some embodiments, the housing comprises two recesses on opposite sides of the housing, and where the apparatus comprises two transparent covers.

Some embodiments of the present methods comprise: providing a handle-sanitization apparatus that comprises a housing, a sponge applicator, and a sanitization fluid absorbed in the sponge applicator; and coupling the handle-sanitization apparatus to the handle of a shopping cart such that the handle extends through the first opening, the passage, and the second opening and the sponge applicator contacts more than half of the cross-sectional perimeter of the handle. Some embodiments further comprise: passing the apparatus longitudinally along a portion of the handle such that a portion of the sanitization fluid is disposed on the handle.

Some embodiments of the present remote control-sanitization apparatuses comprise: a housing having a first end and a second end, the housing defining a first opening through the first end, a second opening through the second end, and a chamber in fluid communication with the first and second openings, the housing configured to open to permit a user to access the chamber; and a fluid-permeable sponge applicator having a first end, a second end, and a length extending between the first and second ends, the sponge applicator defining a passage extending through the sponge applicator and through the first and second ends of the sponge applicator, the passage having a substantially rectangular cross-section; where the apparatus is configured to removably receive the sponge applicator in the chamber (e.g., when the housing is closed) such that the passage is substantially aligned with the first and second openings of the housing so that a remote control can be passed sequentially through the first opening, the passage, and the second opening such that when passed through the passage the sponge applicator contacts more than half of the cross-sectional perimeter of the remote control.

In some embodiments, the passage has a relaxed long inner dimension of between (e.g., about) 1.5 and 2.5 inches, and a relaxed short inner dimension of between (e.g., about) 0.5 and 1.5 inches. In some embodiments, the first and second openings of the housing are each rectangular and have a long inner dimension that is larger than the relaxed long inner dimension of the passage of the sponge applicator and a short inner dimension that is larger than the relaxed short inner dimension of the passage.

Some embodiments further comprise: a display coupled to the housing. In some embodiments, the display comprises a panel configured to receive an information sheet. In some embodiments, the display comprises a liquid-crystal display (LCD) screen.

Some embodiments of the present methods comprise: providing a remote control-sanitization apparatus that comprises: a housing, a sponge applicator, and a sanitization fluid absorbed in the sponge applicator; and passing a remote control through the passage of the sponge applicator such that a portion of the sanitization fluid is disposed on the remote control.

Some embodiments of the present sanitization kits comprise: a housing having a first end and a second end, the housing defining a first opening through the first end, a second opening through the second end, and a chamber in fluid communication with the first and second openings, the housing configured to open to permit a user to access the chamber; and two or more fluid-permeable sponge applicators each having a first end, a second end, and a length extending between the first and second ends, each sponge applicator defining a passage extending through the sponge applicator and through the first and second ends of the sponge applicator, the passage having a substantially rectangular cross-section; where the housing is configured to removably receive the sponge applicator in the chamber (e.g., when the housing is closed) such that the passage is substantially aligned with the first and second openings of the housing so that a remote control can be passed sequentially through the first opening, the passage, and the second opening such that when passed through the passage the sponge applicator contacts more than half of the cross-sectional perimeter of the remote control; and where the housing is configured to removably and interchangeably receive each of the two or more sponge applicators individually.

Some embodiments of the present stylus-sanitization apparatuses comprise: a housing having a first end and a second end, the housing defining a first opening through the first end and a chamber in fluid communication with the first opening, the housing configured to open to permit a user to access the chamber; and a fluid-permeable sponge applicator having a first end, a second end, and a length extending between the first and second ends, the sponge applicator defining a passage extending through at least a portion of the length of the sponge applicator and through the first end of the sponge applicator, the passage having a substantially circular cross-section; where the housing is configured to removably receive the sponge applicator in the chamber such that the passage is substantially aligned with the first opening of the housing so that a stylus can be passed sequentially through the first opening and the passage such that when passed through the passage the sponge applicator contacts more than half of the cross-sectional perimeter of the stylus.

In some embodiments, the passage has a relaxed inner diameter of between (e.g., about) 0.1 and 0.5 inches. In some embodiments, the passage has a relaxed inner diameter of between (e.g., about) 0.2 and 0.4 inches. In some embodiments, the housing further has a second opening through the second end, the passage extends through the first and second ends of the sponge applicator, and the housing is configured to removably receive the sponge applicator in the chamber such that the passage is also substantially aligned with the second opening.

In some embodiments, the apparatus is configured to be coupled to a point-of-sale (POS) device. In some embodiments, the housing is configured to be removably coupled to a POS device. In some embodiments, the apparatus comprises a stand having a base portion configured to be received in a stylus slot of a POS device such that the housing is supported relative to the POS device. In some embodiments, the base portion has a first longitudinal axis, and the passage has a second longitudinal axis that is not parallel to the first longitudinal axis. In some embodiments, the second longitudinal axis is disposed at an angle of between 30 and 60 degrees relative to the first longitudinal axis.

Some embodiments of the present kits comprise: a point of sale (POS) device having a screen configured to receive input via a stylus; and a stylus-sanitization apparatus coupled to the point of sale device (the sanitization apparatus comprising: a housing having a first end and a second end, the housing defining a first opening through the first end and a chamber in fluid communication with the first opening, the housing configured to open to permit a user to access the chamber; and a fluid-permeable sponge applicator having a first end, a second end, and a length extending between the first and second ends, the sponge applicator defining a passage extending through at least a portion of the length of the sponge applicator and through the first end of the sponge applicator, the passage having a substantially circular cross-section; where the housing is configured to removably receive the sponge applicator in the chamber such that the passage is substantially aligned with the first opening of the housing so that a stylus can be passed sequentially through the first opening and the passage such that when passed through the passage the sponge applicator contacts more than half of the cross-sectional perimeter of the stylus).

Some embodiments of the present methods comprise: providing a stylus sanitization apparatus (that comprises: a housing having a first end and a second end, the housing defining a first opening through the first end and a chamber in fluid communication with the first opening, the housing configured to open to permit a user to access the chamber; and a fluid-permeable sponge applicator having a first end, a second end, and a length extending between the first and second ends, the sponge applicator defining a passage extending through at least a portion of the length of the sponge applicator and through the first end of the sponge applicator, the passage having a substantially circular cross-section; where the housing is configured to removably receive the sponge applicator in the chamber such that the passage is substantially aligned with the first opening of the housing so that a stylus can be passed sequentially through the first opening and the passage such that when passed through the passage the sponge applicator contacts more than half of the cross-sectional perimeter of the stylus); and passing a stylus through the passage of the sponge applicator such that a portion of the sanitization fluid is disposed on the pen.

Some embodiments of the present methods comprise: providing a point of sale (POS) device having a screen configured to receive input via a stylus; providing a stylus coupled to the POS device by a flexible tether having a length; and providing a stylus-sanitization apparatus within a distance of the POS device that is less than or substantially equal to the length of the tether, (the sanitization apparatus comprising: a housing having a first end and a second end, the housing defining a first opening through the first end and a chamber in fluid communication with the first opening, the housing configured to open to permit a user to access the chamber; and a fluid-permeable sponge applicator having a first end, a second end, and a length extending between the first and second ends, the sponge applicator defining a passage extending through at least a portion of the length of the sponge applicator and through the first end of the sponge applicator, the passage having a substantially circular cross-section; where the housing is configured to removably receive the sponge applicator in the chamber such that the passage is substantially aligned with the first opening of the housing so that a stylus can be passed sequentially through the first opening and the passage such that when passed through the passage the sponge applicator contacts more than half of the cross-sectional perimeter of the stylus).

Some embodiments of the present kits comprise: a housing having a first end and a second end, the housing defining a first opening through the first end and a chamber in fluid communication with the first opening, the housing configured to open to permit a user to access the chamber; and two or more fluid-permeable sponge applicators each having a first end, a second end, and a length extending between the first and second ends, the sponge applicator defining a passage extending through at least a portion of the length of the sponge applicator and through the first end of the sponge applicator, the passage having a substantially circular cross-section; where the housing is configured to removably receive the sponge applicator in the chamber such that the passage is substantially aligned with the first opening of the housing so that a stylus can be passed sequentially through the first opening and the passage such that when passed through the passage the sponge applicator contacts more than half of the cross-sectional perimeter of the stylus; and where the housing is configured to removably and interchangeably receive each of the two or more sponge applicators individually.

Any embodiment of any of the present methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIGS. 1A-1H and 1J depict various views of an embodiment of a pen-sterilization apparatus, and components of alternative embodiments of sterilization apparatuses.

FIG. 2 depicts a perspective view of a sponge applicator configured for use with the pen-sterilization apparatus of FIGS. 1A-1G.

FIGS. 9A-9C and 10 depict various views of an embodiment of a stylus-sanitization apparatus and of one method of use of the stylus-sanitization apparatus.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps. For example, in an apparatus that comprises a housing and a sponge applicator, the apparatus includes the specified elements but is not limited to having only those elements. For example, such an apparatus could also include a stand coupled to the housing.

Further, a device or structure that is configured in a certain way is configured in at least that way, but it can also be configured in other ways than those specifically described.

Figure 1A:
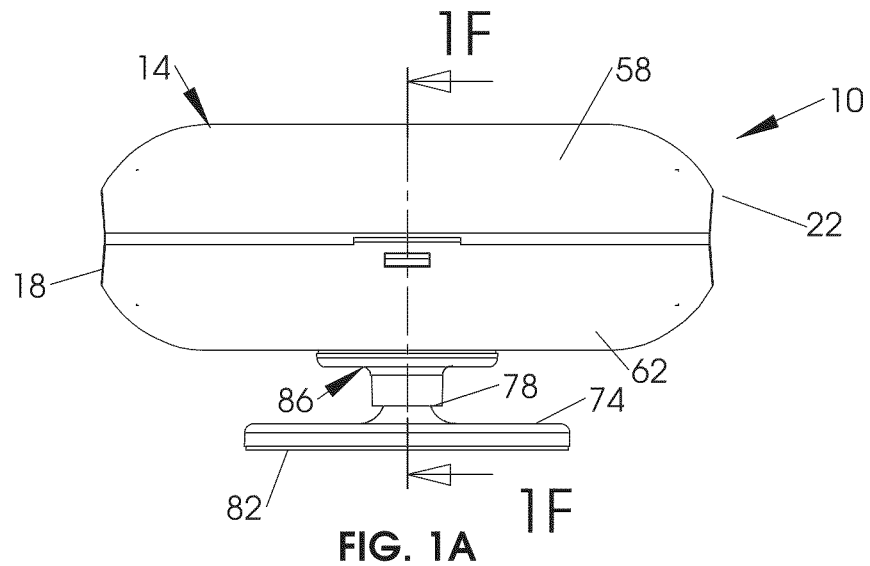
Figure 1B:
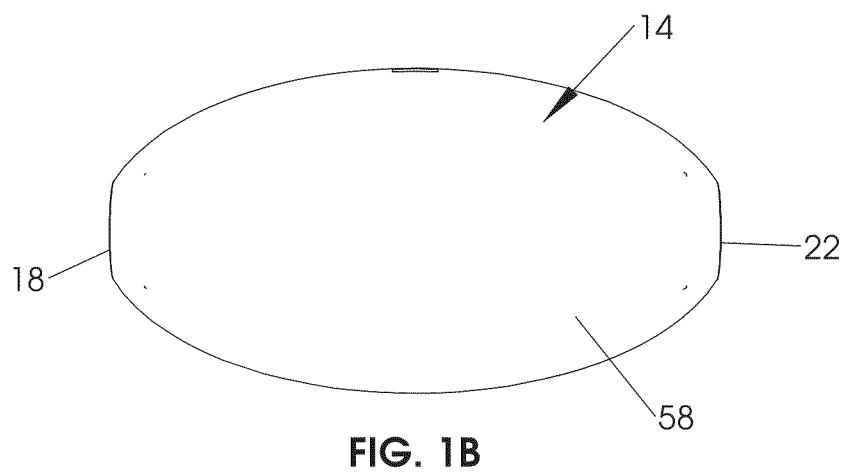
Figure 1C:
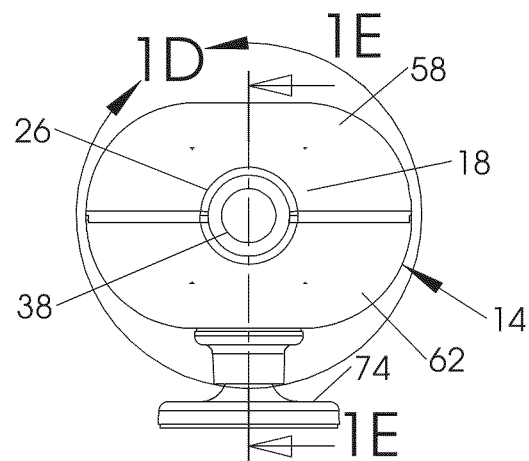
Figure 1D:
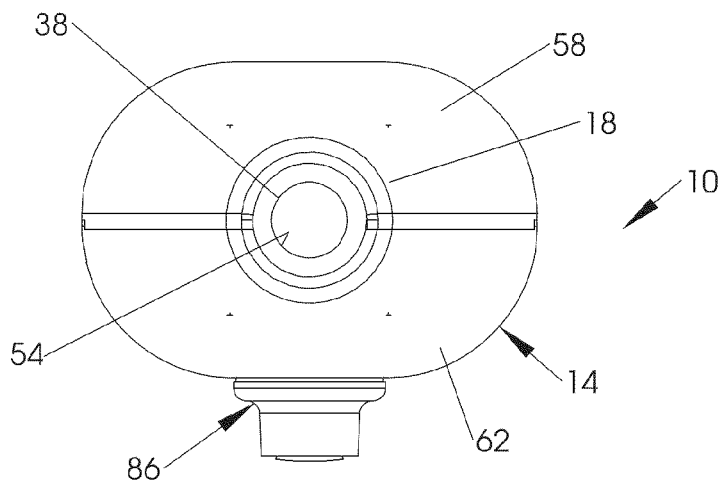
Figure 1E:
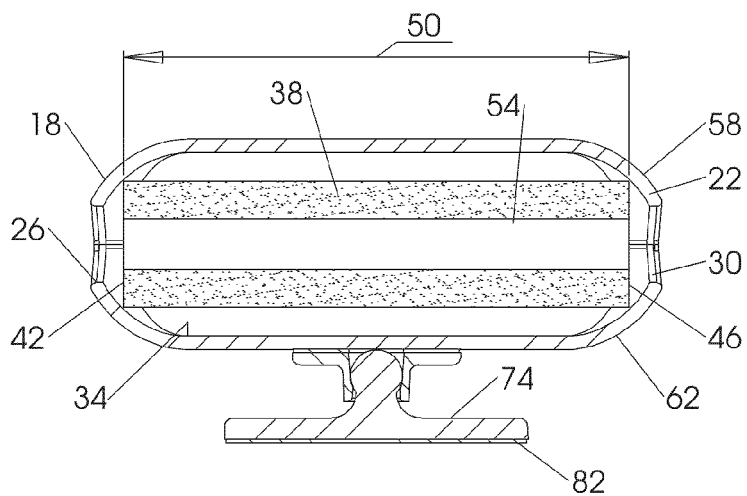
Figure 1F:
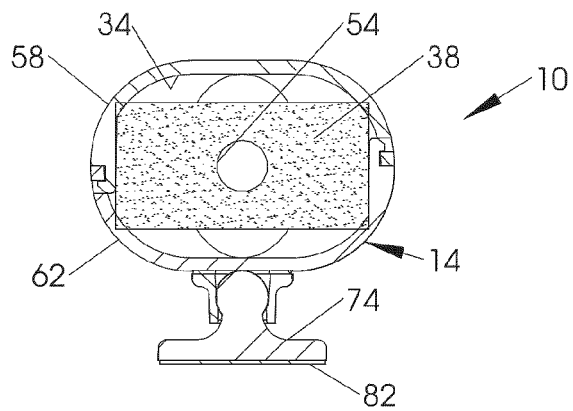

Referring now to the drawings, and more particularly to FIGS. 1A-1G, various views are shown of one embodiment of a pen-sanitization apparatus 10. FIG. 1A depicts a side view of apparatus 10; FIG. 1B depicts a top view of apparatus 10; FIG. 1C depicts an end view of apparatus 10; FIG. 1D depicts an enlarged end view of apparatus 10 taken within circle 1D of FIG. 1C; FIG. 1E depicts a cross-sectional view of apparatus 10 taken along line 1E-1E of FIG. 1C; FIG. 1F depicts a cross-sectional view of apparatus 10 taken along line 1F-1F of FIG. 1A; and FIG. 1G depicts an exploded side view of apparatus 10. Additionally, FIG. 1H depicts a front view of an end member for alternative embodiments of apparatus 10; and FIG. 1J depicts a front view of another end member for alternative embodiments of apparatus 10.

In the embodiment shown, pen-sanitization apparatus 10 comprises a housing 14 having a first end 18 and a second end 22. Housing 14 housing defines a first opening 26 through first end 18, a second opening 30 through second end 22, and a chamber 34 in fluid communication with first and second openings 26 and 30. Housing 14 is also configured to open to permit a user to access chamber 34, as shown in FIG. 1G. Pen-sanitization apparatus 10 also comprises a fluid-permeable sponge applicator 38 having a first end 42, a second end 46, and a length 50 extending between first and second ends 42 and 46. Sponge application 38 can comprise, for example, a foam (e.g., an antimicrobial, open-cell polyurethane foam). Sponge applicator 38 defines a passage 54 extending through sponge applicator 38 and through first and second ends 42 and 46 of the sponge applicator. In the embodiment shown, passage 54 has a substantially circular cross-section, as shown. In other embodiments, passage 54 can have any suitable cross-sectional shape, such as, for example, square, rectangular, triangular, oval, fanciful or irregular, and/or the like. Housing 14 is configured to removably receive sponge applicator 38 in chamber 34 (e.g., when the housing is closed, as shown in FIGS. 1E and 1F) such that passage 54 is substantially aligned with the first and second openings 26 and 30 of the housing (e.g., as shown in FIG. 1E) so that a pen can be passed sequentially through first opening 26, passage 54, and second opening 30 such that when passed through passage 54 sponge applicator 38 contacts more than half of the cross-sectional perimeter of the pen (i.e., the outer perimeter of a cross-section of the pen taken perpendicular to the longitudinal axis of the pen at a point along the length of the pen).

In the embodiment shown, passage 54 has a relaxed inner diameter (e.g., a diameter when the sponge applicator and passage 54 are in a relaxed or un-stretched configuration) of between (e.g., about) 0.1 and 0.5 inches, and/or between (e.g., about) 0.2 and 0.4 inches. In some embodiments, the relaxed inner diameter of passage 54 is equal to, less than, greater than, or between any of (e.g., about): 0.1, 0.15, 0.2, 0.25, 0.3, 0.35, 0.4, and 0.45 inches. In the embodiment shown, sponge applicator 38 encircles the entire length of passage 54. Additionally, apparatus 10 is configured such that pens having various diameters within a functional range can be passed sequentially through the first opening, passage, and second opening such that when passed through the passage the sponge applicator contacts more than half of the cross-sectional perimeter of the pen (e.g., contacts up to the entire cross-sectional perimeter of at least a portion of the pen). More particularly, in the embodiment shown, first and second openings 26 and 30 are each circular and have a diameter that is larger than the relaxed inner diameter of passage 54 through the sponge applicator. In this way, pens having a diameter larger than the relaxed inner diameter of passage 54 can be passed through first and second openings 26 and 30 such that the sponge applicator (e.g., passage 54) can expand (and subsequently contract) to fit pens having a variety of diameters (e.g. within a "functional range" between, e.g., the minimum dimension of first and second openings 26 and 30 and the relaxed diameter of passage 38). In the embodiment shown, the functional range is between (e.g., about) 0.2 inches and 0.4 inches.

In the embodiment shown, apparatus 10 further comprises a sanitization fluid absorbed in the sponge applicator. In many embodiments, the sanitization fluid comprises a liquid. In some embodiments, the sanitization fluid comprises a gel (e.g., a gel that is configured or formulated to resist evaporation. The sanitization fluid can comprise, for example, one or more ingredients selected from the group consisting of: alcohols, ethanol, isopropanol, aldehydes, oxidizing agents, acids, phenolics, ammoniums, and chlorine. One example of a sanitization fluid suitable for some of the present embodiments is benzalkonium chloride (BZK), such as, for example, a solution with equal to, less than, or between any of: 0.1, 0.13, 0.15, 0.2, and/or 0.26 percent by weight of benzalkonium chloride. In the embodiment shown, apparatus 10 does not comprise a pump mechanism, and instead, is configured such that if the sponge applicator is disposed in the chamber and a pen is passed sequentially through first opening 26, passage 54, and second opening 30 (or second opening 30, passage 54, and first opening 26), the sanitization fluid is applied to the pen by the sponge applicator without any external pumping mechanism.

In the embodiment shown, housing 14 comprises an first (e.g., upper) housing member 58 and a second (e.g., lower) housing member 62, and is configured to open by separating a portion (up to all) of upper housing member 58 from a portion (up to all) of lower housing member 62. In the embodiment shown, lower housing member 62 is configured to be coupled to upper housing member 58 (e.g., by way of tabs 66 and corresponding slots 70) to define chamber 34 and to be separated from upper housing member 58 to permit a user to access chamber 34. In other embodiments, upper housing member 58 is pivotally coupled to lower housing member 62.

In the embodiment shown, apparatus 10 further comprises: a mount or stand 74 having a first end 78 coupled to the housing and a second end 82 configured to be coupled to a surface such that the stand supports the apparatus. More particularly, in the embodiment shown, first end 78 is configured to be pivotally coupled to the housing (e.g., bottom housing member 62) such as, for example, by way of a ball joint 86. In some embodiments, the stand (e.g., second end 82 of the stand) comprises an adhesive (e.g., such that second end 82 can be attached to a surface). In other embodiments, second end 82 comprises a suction cup.

In some embodiments, first and second ends 42 and 46 of sponge applicator 38 are configured to be fluid-impermeable. For example, in some embodiments, first and second ends 42 and 46 of the sponge applicator are coated with a fluid-impermeable material. In some embodiments, the outer surface of the sponge applicator between the first and second ends (e.g., all of the outer surface external to passage 54) are coated with a fluid impermeable material. Fluid-impermeable material can comprise, for example, one or more materials selected from the group consisting of paints, lacquers, polymers, plastics, and the like. Another example of a fluid-impermeable material is a polyurethane solution (e.g., with a vinyl solvent base), such as, for example, PDC.RTM F-874 MURACULON, available from PLASTI DIP INTERNATIONAL, USA). In this way, the sponge applicator can be configured to resist evaporation of sanitization fluid from the sponge applicator and/or may remove excess sanitization fluid from a pen as it is passed out of the apparatus.

In other embodiments, the apparatus further comprises two end members 90a each coupled to the housing (e.g., housing 14) adjacent a different one of the first and second openings (e.g., each coupled to an inner surface of the housing adjacent to one of first and second openings 26 and 30) of the housing such that the end member covers a portion of the coupled opening. In some such embodiments, end members 90a are each resilient and configured such that if a pen is passed through the respective one of the first and second openings of the housing, the end member will deform to permit the pen to pass through the opening such that the pen contacts the end member as the pen passes through the opening. In some such embodiments, the end members (e.g., end members 90b) are each configured to substantially cover the respective one of the first and second openings when a pen is not passed through the respective opening. More particularly, end members 90b each comprise a resilient flap having one or more slits defining a plurality of subflaps 94 and are configured such that if a pen is passed through the respective opening of the housing, subflaps 94 will move apart as the pen passes through the end member and will move together when the pen is removed from the end member.

Some embodiments of the present kits comprise a housing 14; and two or more (e.g., two, three, four, five, six, seven, eight, nine, ten, or more) fluid-permeable sponge applicators 38, where the housing is configured to removably and interchangeably receive each of the two or more sponge applicators individually (e.g., such that housing can receive a first one of the sponge applicators, the first one of the sponge applicators can be removed from the housing, and the housing can receive another one of the sponge applicators). For example, in some embodiments, the kit further comprises a sanitization fluid absorbed in each of the sponge applicators. In some embodiments, the sponge applicators are preloaded with the sanitization fluid. For example, FIG. 2 illustrates a sponge applicator 38 that is preloaded with sanitization fluid and is sealed in a capsule 96 that is impermeable to fluid and/or gas to prevent the sanitization fluid from evaporating out of the sponge applicator 38. As shown in FIG. 2, in some embodiments of the present apparatuses, kits, and methods, sponge applicator 38 has a rectangular cross-section and/or has chamfered corners 98. In other embodiments, sponge applicator has a rectangular cross section (e.g., transverse to passage 54) and curved sides (e.g., extending between rectangular ends 42 and 46).

Figure 3A:
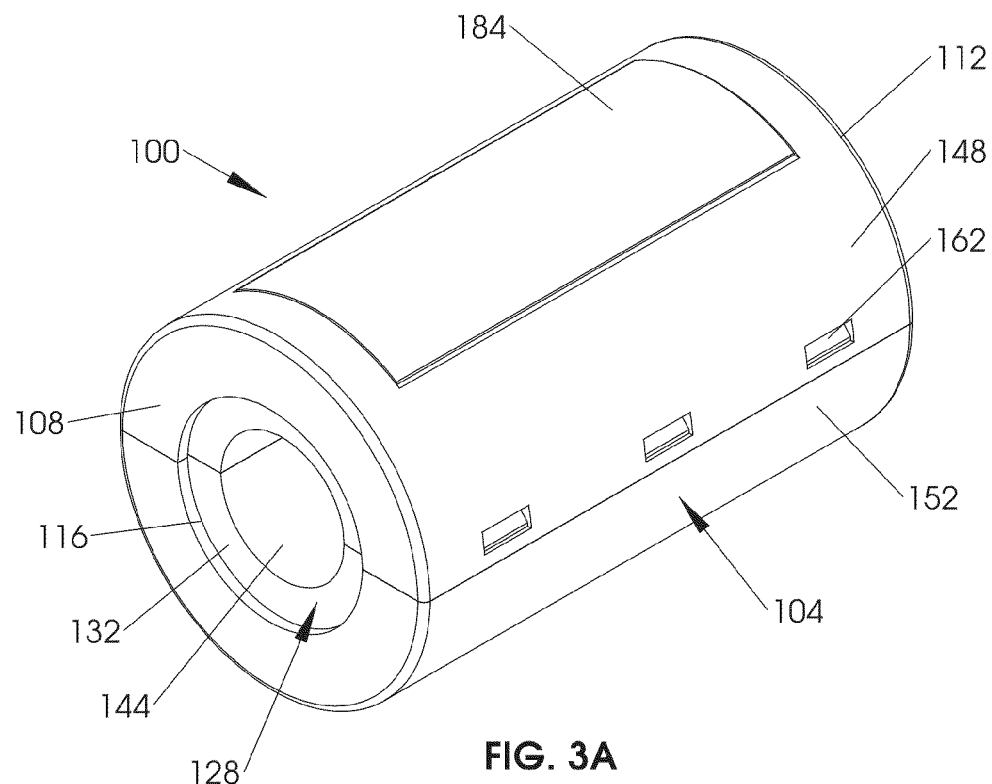
FIGS. 3A-3E depict various views of one embodiment of a handle-sterilization apparatus.
Figure 3B:
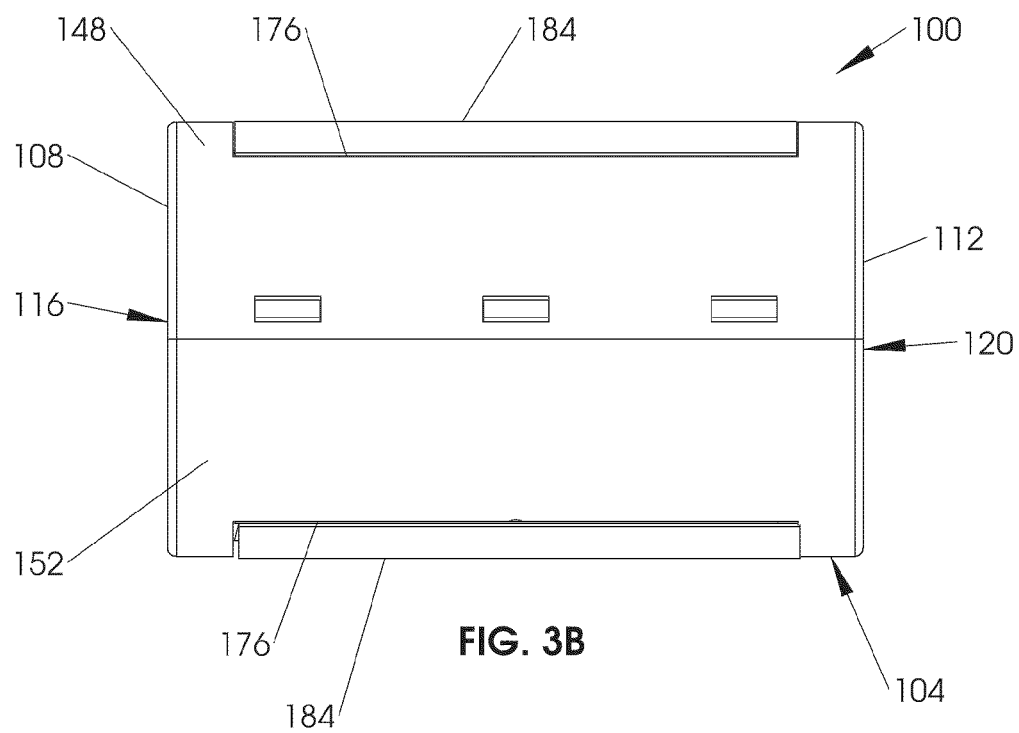
Figure 3C:
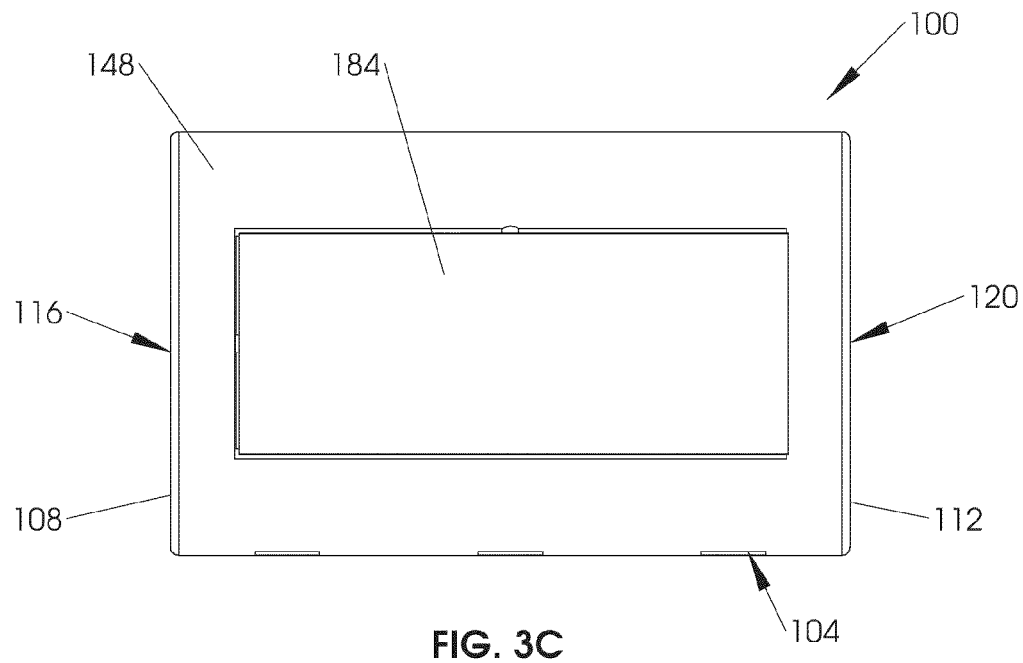
Figure 3D:
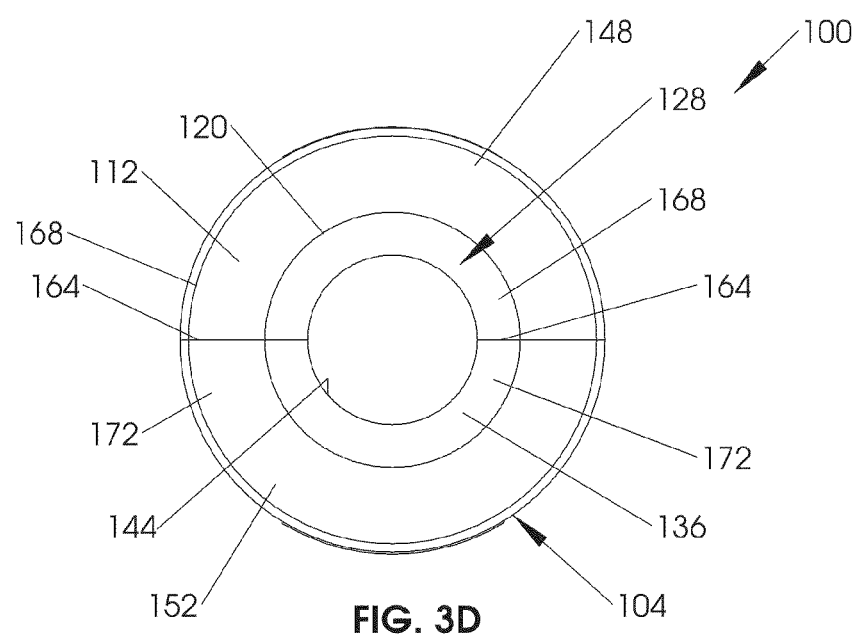
Figure 3E:
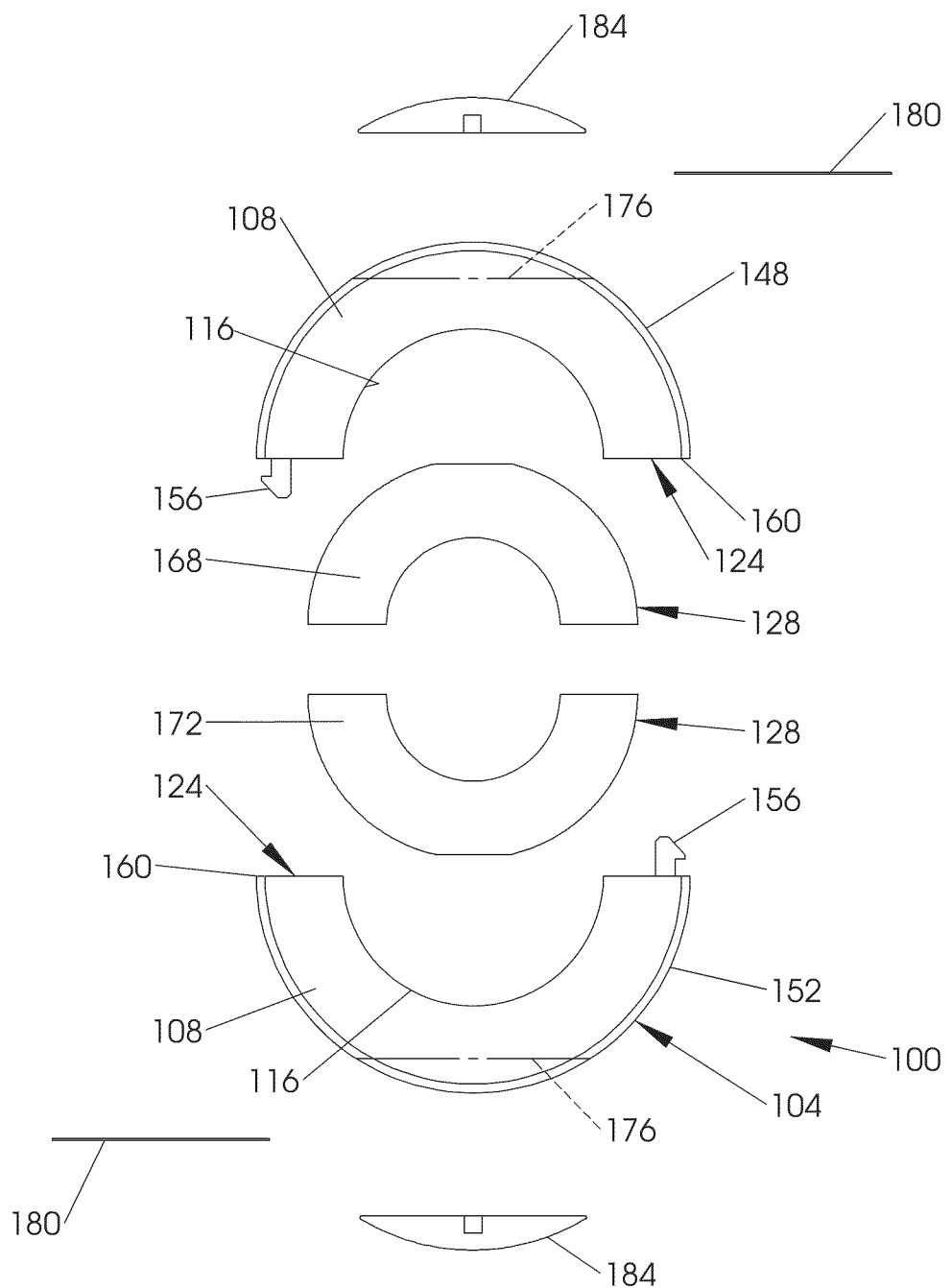

Referring now to FIGS. 3A-3E, various views are shown of one embodiment of a handle-sanitization apparatus 100. FIG. 3A depicts a perspective view of apparatus 100; FIG. 3B depicts a side view of apparatus 100; FIG. 3C depicts a top view of apparatus 100; FIG. 3D depicts an end view of apparatus 100 depicts an end view of apparatus 100; and FIG. 3E depicts an exploded end view of apparatus 100.

In the embodiment shown, apparatus 100 comprises: a housing 104 having a first end 108 and a second end 112. Housing 104 defines a first opening 116 through first end 108, a second opening 120 through second end 112, and a chamber 124 in fluid communication with first and second openings 116 and 120. In the embodiment shown, apparatus 100 also comprises a fluid-permeable sponge applicator 128 having a first end 132, a second end 136, and a length 140 extending between first and second ends 132 and 136. Sponge applicator 128 defines a passage 144 extending through sponge applicator 128 and through first and second ends 132 and 136 of the sponge applicator. In the embodiment shown, passage 144 has a substantially circular cross-section defined by a relaxed inner diameter (e.g., a diameter when the sponge applicator and passage 144 are in a relaxed or un-stretched configuration). In other embodiments, passage 144 can have any suitable cross-sectional shape, such as, for example, square, rectangular, triangular, oval, fanciful or irregular, and/or the like. Apparatus 100 is configured to be removably coupled to a handle (e.g., a shopping cart handle or other elongated handle) such that the handle extends through first opening 116, passage 144, and second opening 120 and the sponge applicator contacts more than half of the (up to the entire) cross-sectional perimeter of the handle. The relaxed inner diameter of passage 144 can be, for example, between (e.g., about) 1 and 2 inches, between (e.g., about) 1.3 and 1.7 inches, and/or equal to (e.g., about) 1.5 inches. As with the embodiments described above, apparatus 100 can comprise a sanitization fluid (e.g., absorbed in sponge applicator 128, and/or separately packaged for loading or absorbing into a sponge applicator).

In the embodiment shown, first and second openings 116 and 120 of the housing each have a minimum inner dimension that is larger than the relaxed inner diameter of passage 144 through the sponge applicator. In this way, apparatus 100 can be removably coupled to handles having various diameters within a functional range such that the sponge applicator contacts more than half of the cross-sectional perimeter of the handle (e.g., contacts up to the entire cross-sectional perimeter of at least a portion of the handle). For example, apparatus 100 can be removably coupled to handles having a diameter larger than the relaxed inner diameter of passage 144 such that the sponge applicator (e.g., passage 144) can expand (and subsequently contract) to fit pens having a variety of diameters (e.g. within a "functional range" between, e.g., the minimum dimension of first and second openings 116 and 120 and the relaxed diameter of passage 144). In the embodiment shown, the functional range is between (e.g., about) 1 and 2 inches, between (e.g., about) 1.3 and 1.7 inches, and/or (e.g., about) 1.5 inches. In some embodiments, the minimum inner dimension of each of first and second openings 116 and 120 can be between (e.g., about) five (5) percent and fifty (50) percent larger than the relaxed inner diameter of the passage, between (e.g., about) twenty (20) percent and thirty (30) percent larger than the relaxed inner diameter of the passage, and/or at least ten (10) percent larger than the relaxed inner diameter of the passage.

In the embodiment shown, housing 104 comprises an upper housing member 148 and a lower housing member 152 configured to be coupled to upper housing member 148 (e.g., by way of tabs 156 and corresponding slots 160) to define chamber 124 and configured to be separated from upper housing member 148 to permit a user to access chamber 124. In some embodiments, sponge applicator 128 comprises a slit 164 extending between first and second ends 132 and 136 of sponge applicator 128 such that the sponge applicator can be wrapped around a handle such that the handle is disposed in passage 144. In the embodiment shown, sponge applicator 128 comprises and upper sponge portion 168 and lower sponge portion 172 divided by two slits 164 such that upper and lower sponge portions 168 and 172 can be sandwiched around a handle and upper and lower housing portions 148 and 152 coupled to one another around the upper and lower sponge portions.

In some embodiments, housing 104 further comprises one or more recesses 176 each configured to receive an insert 180, and apparatus 104 comprises one or more transparent covers 184 each configured to be removably coupled to the housing such that the cover substantially encloses the recess and will retain an insert 180 in the recess. For example, in the embodiment shown, housing 104 comprises two recesses 176 on opposite sides of the housing (e.g., one recess 176 on upper housing member 148 and one recess 176 on lower housing member 152) and apparatus 104 comprises two transparent covers 184 each configured to be removably coupled to the housing such that the cover substantially encloses the recess and will retain an insert 180 in the recess. Inserts 180 can comprise, for example, text, images, and/or the like (e.g., for advertising, coupons, and/or the like). In the embodiment shown, recesses 176 each have a substantially planar bottom (e.g., to reduce perceived warping or perceived parallax differences of the inserts). In the embodiment shown, transparent covers 184 each have an arcuate outer surface shaped to match the external contour of the housing.

Figure 4A:
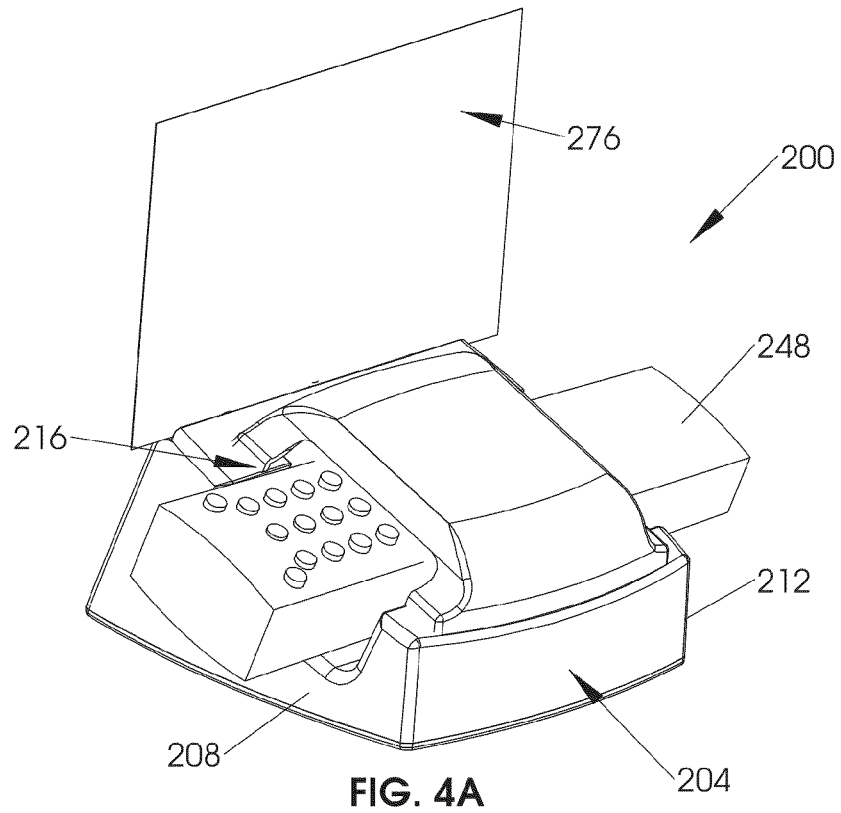
FIGS. 4A-4E depicts various views of one embodiment of a remote control-sterilization apparatus.
Figure 4B:
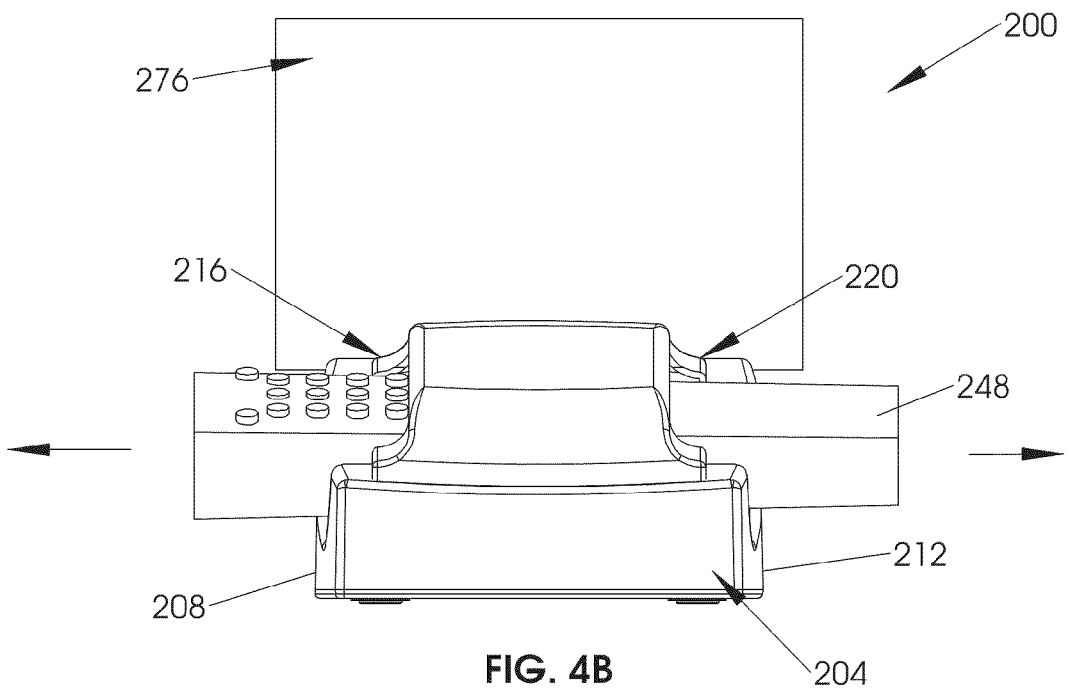
Figure 4C:
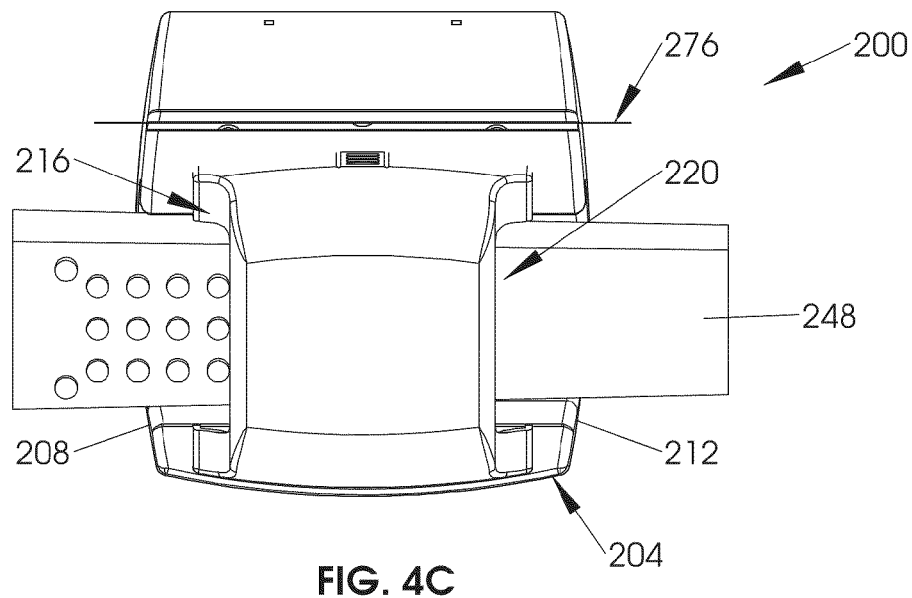
Figure 4D:
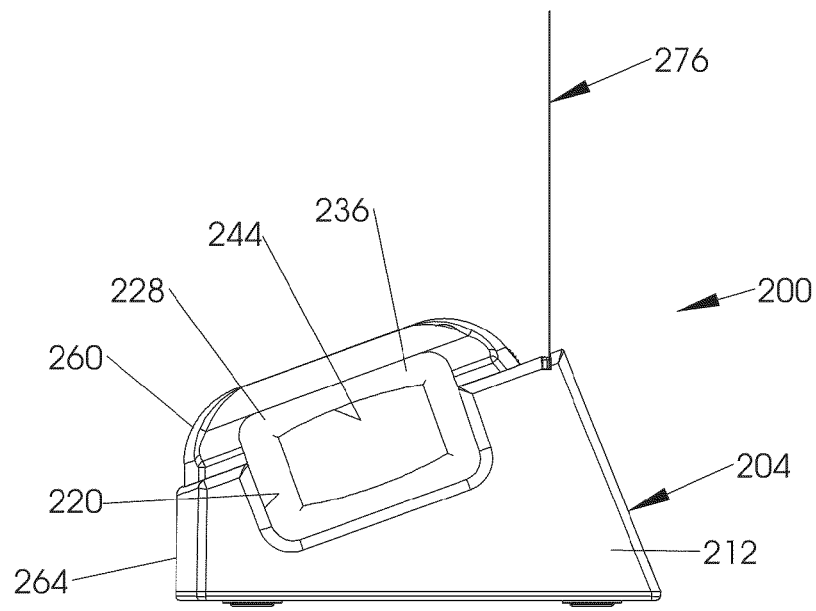
Figure 4E:
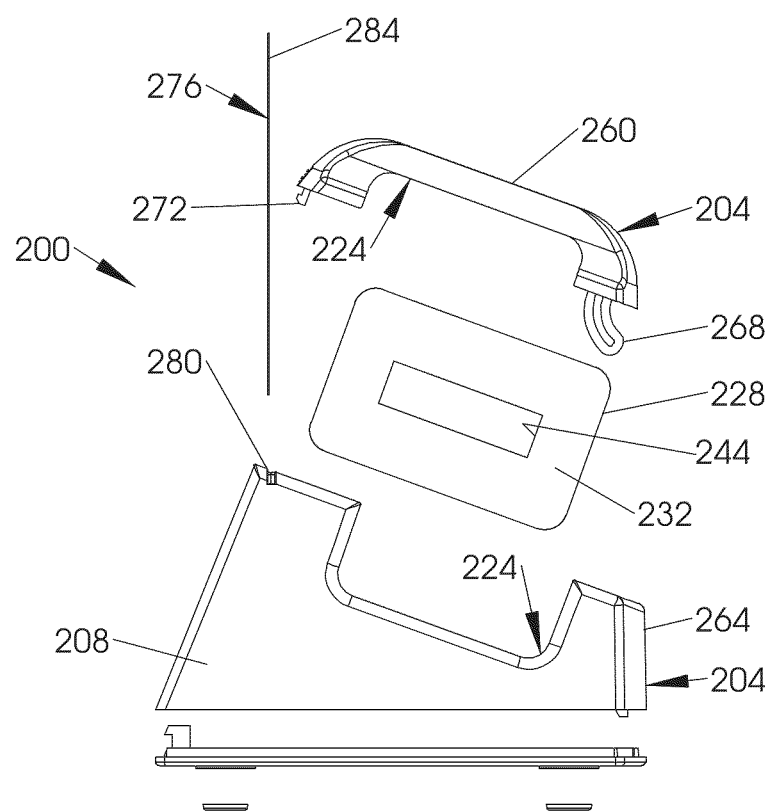

Referring now to FIGS. 4A-4E, various views are shown of one embodiment of a remote control-sanitization apparatus and/or pager-sanitization apparatus 200. FIG. 4A depicts an upper perspective view of apparatus 200; FIG. 4B depicts a front view of apparatus 200; FIG. 4C depicts a top view of apparatus 200; FIG. 4D depicts a side view of apparatus 200; and FIG. 4E depicts an exploded side view of apparatus 200.

In the embodiment shown, remote control-sanitization apparatus 200 comprises a housing 204 having a first end 208 and a second end 212. Housing 204 defines a first opening 216 through first end 208, a second opening 220 through second end 212, and a chamber 224 in fluid communication with first and second openings 216 and 220. Housing 204 is also configured to open to permit a user to access chamber 224. In the embodiment shown, apparatus 200 also comprises a fluid-permeable sponge applicator 228 having a first end 232, a second end 236, and a length 240 extending between first and second ends 232 and 236. Sponge applicator 228 defines a passage 244 extending through sponge applicator 228 and through first and second ends 232 and 236 of the sponge applicator. In the embodiment shown, passage 244 has a substantially rectangular cross-section. As such, passage 244 has a relaxed long inner dimension and a relaxed short inner dimension. In some embodiments, passage 244 has a relaxed long inner dimension of between (e.g., about) 1.5 and 3.5 inches (e.g., e.g., equal to, less than, greater than, or between any of (e.g., about): 1.5, 1.75, 2.0, 2.25, 2.5, 2.75, 3.0, 3.25, and 3.5 inches), and a relaxed short inner dimension of between (e.g., about) 0.5 and 2.5 inches (e.g., equal to, less than, greater than, or between any of (e.g., about) 0.5, 0.75, 1.0, 1.25, 1.5, 1.75, 2.0, 2.25, and 2.5 inches). As with the embodiments described above, apparatus 200 can comprise a sanitization fluid (e.g., absorbed in sponge applicator 228, and/or separately packaged for loading or absorbing into a sponge applicator).

In the embodiment shown, apparatus 200 is configured such that remote controls and/or pagers (e.g., restaurant pagers) having various cross-sectional dimensions within a functional range can be passed sequentially through the first opening, passage, and second opening such that when passed through the passage the sponge applicator contacts more than half of the cross-sectional perimeter of the remote control (e.g., contacts up to the entire cross-sectional perimeter of at least a portion of the remote control). More particularly, in the embodiment shown, first and second openings 216 and 220 are each rectangular and have a long inner dimension that is larger than the relaxed long inner dimension of passage 244 and a short inner dimension that is larger than the relaxed short inner dimension of passage 244. In this way, remote controls having long and short cross-sectional dimensions larger than the relaxed long and short dimensions of passage 244 can be passed through first and second openings 216 and 220 such that the sponge applicator (e.g., passage 244) can expand (and subsequently contract) to fit remote controls having a variety of cross-sectional dimensions (e.g. within a "functional range" between, e.g., the dimensions of first and second openings 216 and 220 and the relaxed inner dimensions of passage 244.

In some embodiments, the minimum inner dimension of each of first and second openings 216 and 220 can be between (e.g., about) five (5) percent and fifty (50) percent larger than the corresponding relaxed inner dimensions of passage 244, between (e.g., about) twenty (20) percent and thirty (30) percent larger than corresponding relaxed inner dimensions of the passage, and/or at least ten (10) percent larger than the corresponding relaxed inner dimensions of the passage. In some embodiments, passage 244 has a relaxed long inner dimension of between (e.g., about) 1.5 inches and 3.5 inches (e.g., e.g., equal to, less than, greater than, or between any of (e.g., about): 1.5, 1.75, 2.0, 2.25, 2.5, 2.75, 3.0, 3.25, and 3.5 inches), and a relaxed short inner dimension of between (e.g., about) 0.5 and 2.5 inches (e.g., equal to, less than, greater than, or between any of (e.g., about): 0.5, 0.75, 1.0, 1.25, 1.5, 1.75, 2.0, 2.25, and 2.5 inches). For example, in one embodiment, openings 216 and 220 have a long and short inner dimensions of 2.5 inches and 1.5 inches, respectively; and passage 244 has relaxed long and short inner dimensions of 1.75 inches and 0.5 inches, respectively.

In some embodiments, sponge applicator 228 is provided with one or more protrusions or bumps (not shown) that extend into passage 244 (e.g., from the upper or lower long surface of the sponge applicator within passage 244). For example, such protrusions can be provided or configured with ends that have a round, square, or pointed shape such that the protrusions can extend between the keys or buttons of a remote control.

Housing 204 is configured to removably receive sponge applicator 228 in chamber 224 (e.g., when the housing is closed) such that passage 244 is substantially aligned with first and second openings 216 and 220 of the housing so that a remote control 250 can be passed sequentially through first opening 216, passage 244, and second opening 220 (e.g., as shown) such that when passed through passage 244 the sponge applicator contacts more than half of the cross-sectional perimeter of the remote control 248. For example, remote control 248 can be passed through passage 244 in first direction 252 or second direction 256.

In the embodiment shown, housing 204 comprises an upper housing member 260 and a lower housing member 264 configured to be coupled to upper housing member 260 (e.g., by way of a slotted member 268 and tab 272) to define chamber 224 and configured to be separated from upper housing member 260 to permit a user to access chamber 224. More particularly, in the embodiment shown, slotted member 268 is provided with an arcuate shape such that when upper housing member 260 is coupled to lower housing member 264, upper housing member 260 can move (e.g., pivot) relative to lower housing member 264 without being completely removed from lower housing member 264 to enable replacement and/or replenishment (refilling) of sponge applicator 228.

In the embodiment shown, apparatus comprises a display 276. Display 276 includes a slot or notch 280 in housing 204 (e.g., lower housing member 264) and a panel 284. Panel 284 is configured to receive an information sheet. For example, panel 284 can comprise two transparent sheets (e.g., plexi-glass, glass, polycarbonate, etc.), one transparent and one non-transparent sheet, or the like between which a printed sheet can be sandwiched or positioned to hold the printed sheet in a position that is easily viewable by a user. Display 276 can hold, for example, a channel listing, a listing of current pay-per-view movies, a listing of services available through a television or other system controlled by a remote-control, and/or any other advertisement or printed information.

Some embodiments of the present kits comprise a housing 204; and two or more (e.g., two, three, four, five, six, seven, eight, nine, ten, or more) fluid-permeable sponge applicators 228, where the housing is configured to removably and interchangeably receive each of the two or more sponge applicators individually (e.g., such that housing can receive a first one of the sponge applicators, the first one of the sponge applicators can be removed from the housing, and the housing can receive another one of the sponge applicators). For example, in some embodiments, the kit further comprises a sanitization fluid absorbed in each of the sponge applicators (e.g., the sponge applicators can be preloaded with the sanitization fluid).

Figure 5:
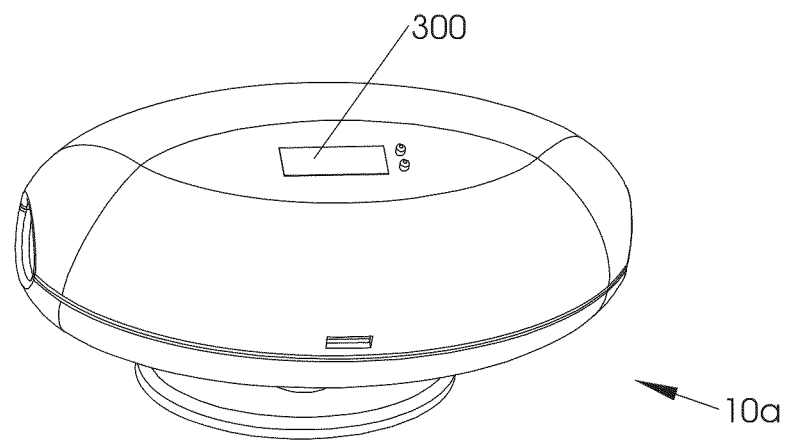
FIG. 5 depicts a perspective view of another embodiment of a pen-sterilization apparatus.

Referring now to FIG. 5, an alternative embodiment is shown of apparatus 10. More particularly, apparatus 10a comprises a liquid crystal display (LCD) screen 300 that can be configured to display the time (e.g., LCD screen 300 can be coupled to or integral to a clock). In other embodiments, LCD screen 300 can be configured display any suitable information. For example, LCD screen 300 can be coupled to or integral to a counter that counts (e.g., either up or down) the number of times a pen has been sanitized with apparatus 10a and/or displays when the sponge applicator is expected to need refilling or replacement. By way of another example, LCD screen 300 can be coupled to a humidity sensor inside the housing to indicate when low humidity indicates that sponge applicator may need refilling or replacement.

Figure 6:
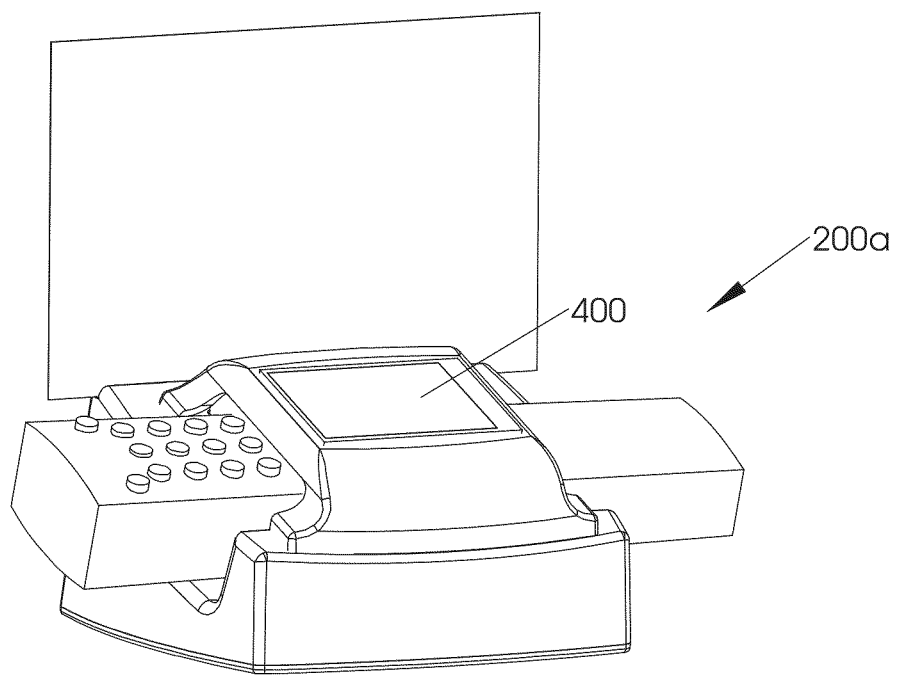
FIG. 6 depicts a perspective view of another embodiment of a remote control-sterilization apparatus.

Referring now to FIG. 6, an alternative embodiment is shown of apparatus 200. More particularly, apparatus 200a comprises a liquid crystal display (LCD) screen 304 that is larger than LCD screen 300. LCD screen 400 can be configured to display any suitable information, and/or can be a touch-screen. For example, LCD screen 400 can be configured to display a television schedule, hotel checkout information, receive and display credit card information for a user to enable payment (e.g., for hotel services such as room service), and/or any other suitable information.

Figure 7:
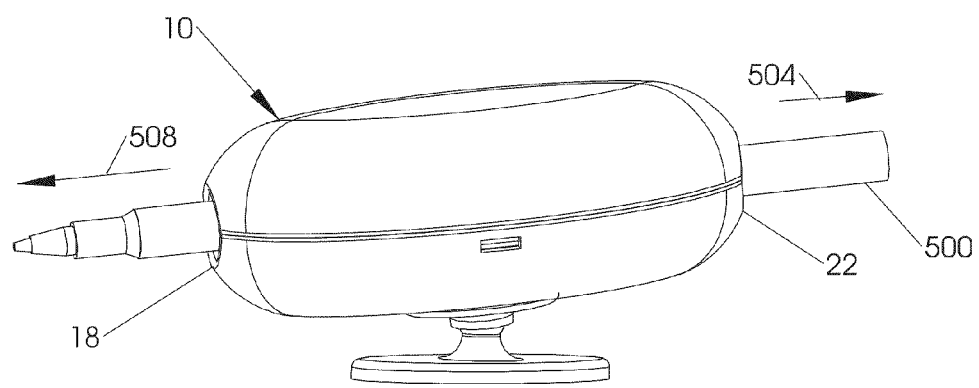
FIG. 7 depicts a perspective view of one method of use of the pen-sanitization apparatus of FIGS. 1A-1G.

Referring now to FIG. 7, a perspective view is shown of one method of use of pen-sanitization apparatus 10 of FIGS. 1A-1G. In the embodiment shown, the method comprises: providing a pen sanitization apparatus 100 comprising: housing 14, sponge applicator 38, and a sanitization fluid absorbed in the sponge applicator; where the sponge applicator is disposed in the chamber of the housing with the passage substantially aligned with first and second openings 18 and 22 of the housing so that a pen (e.g., 500) can be passed sequentially through the first opening, the passage, and the second opening such that when passed through the passage the sponge applicator contacts more than half of the cross-sectional perimeter of pen (e.g., 500). In the embodiment shown, the method further comprises passing a pen 500 through the passage of the sponge applicator such that a portion of the sanitization fluid is disposed on pen 500. Pen 500 can be passed through the passage in first direction 504 and/or second directions 508.

Figure 8:
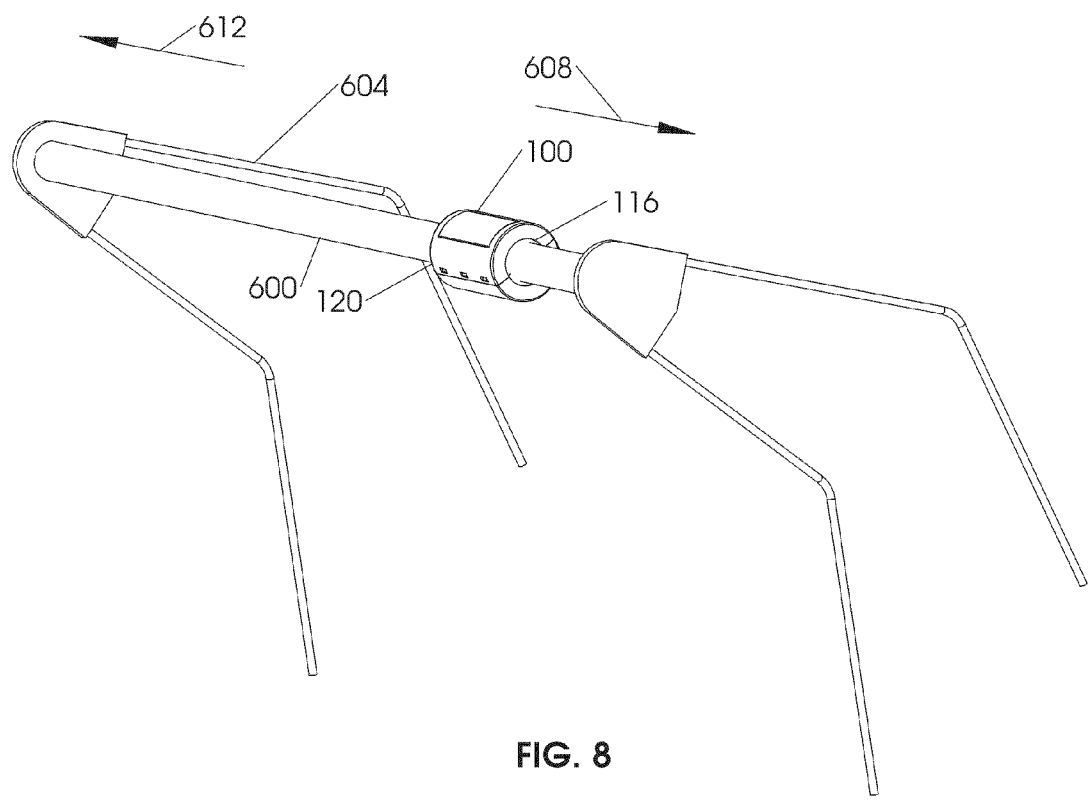
FIG. 8 depicts a perspective view of one method of use of the handle-sanitization apparatus of FIGS. 3A-3E.

Referring now to FIG. 8, a perspective view is shown of one method of use of handle-sanitization apparatus 100 of FIGS. 3A-3E. In the embodiment shown, the method comprises: providing a handle-sanitization apparatus 100 that comprises: housing 104, fluid-permeable sponge applicator 128, and a sanitization fluid absorbed in the sponge applicator, where the first and second openings of the housing each have a minimum inner dimension that is larger than the relaxed inner diameter of the passage through the sponge applicator; and where the apparatus is configured to be removably coupled to a handle (e.g., 600) such that the handle extends through the first opening, the passage, and the second opening and the sponge applicator contacts more than half of the cross-sectional perimeter of the handle. In the embodiment shown, the method further comprises coupling handle-sanitization apparatus 100 to a handle 600 of a shopping cart 604 such that handle 600 extends through first opening 116, the passage, and second opening 120 and the sponge applicator contacts more than half of the cross-sectional perimeter of handle 600. In some embodiments, the method further comprises: passing apparatus 100 longitudinally along a portion of handle 600 such that a portion of the sanitization fluid is disposed on handle 600. Apparatus 100 can be passed along handle 600 in first direction 608 and/or second directions 612.

Figure 9A:
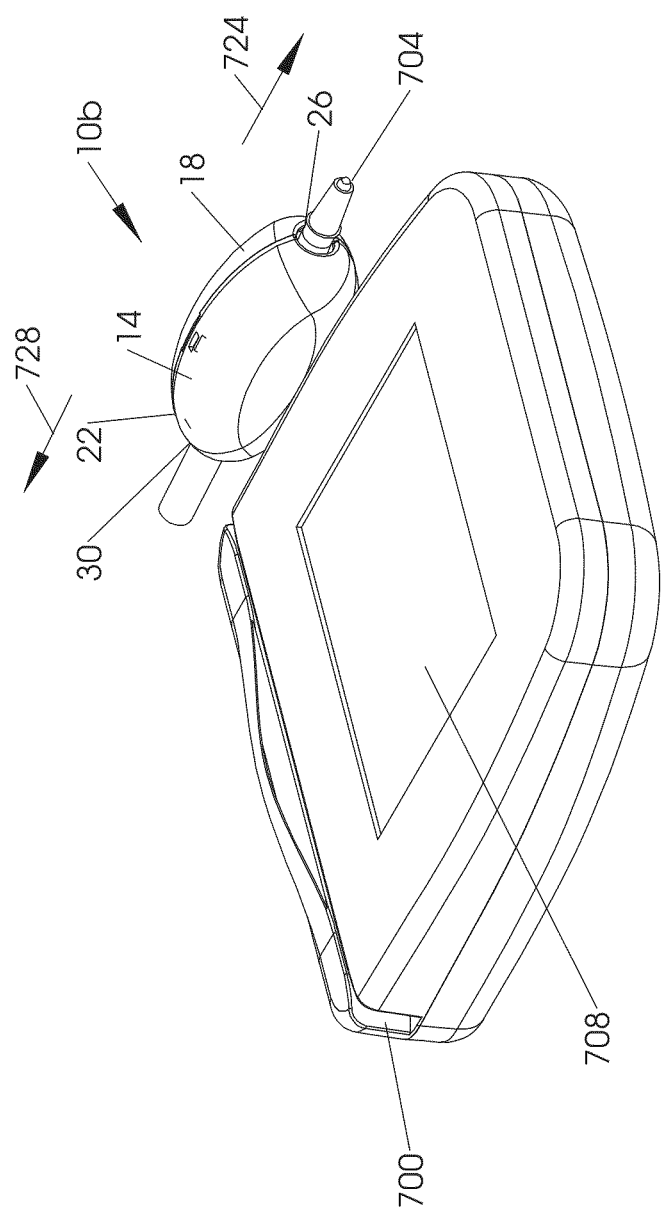
Figure 10:
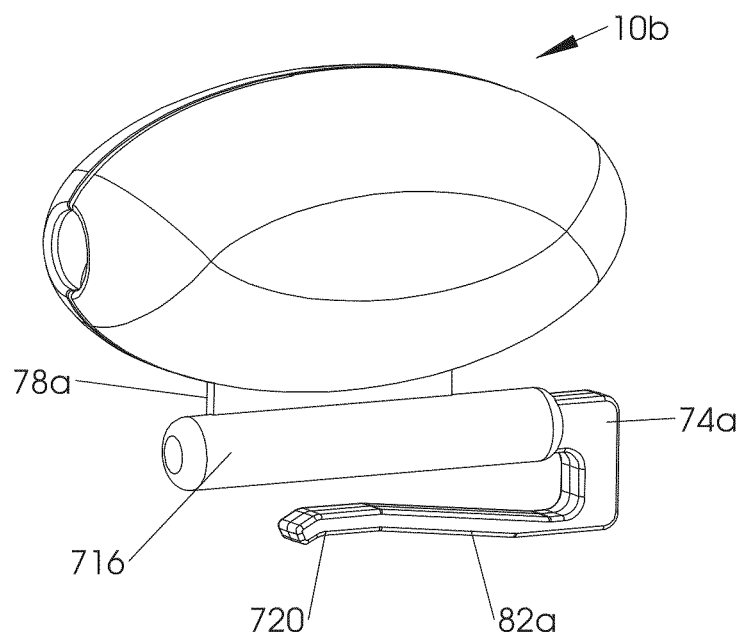

Referring now to FIGS. 9A-9C and 10, various views are shown of a stylus-sanitization apparatus 10b. FIG. 9A depicts a side perspective view of apparatus 10b coupled to a point-of-sale (POS) device 700; FIG. 9B depicts a top perspective view of apparatus 10b coupled to POS device 700; FIG. 9C depicts another side perspective view of apparatus 10b coupled to POS device 700; and FIG. 10 depicts a side perspective view of apparatus 10b alone.

Apparatus 10b is substantially similar to apparatus 10 of FIGS. 1A-1G. For example, apparatus 10b comprises: a housing 14 having a first end 18 and a second end 22; housing 14 defines a first opening 26 through first end 22 and a chamber (see, e.g., chamber 34 of FIGS. 1E and 1F) in fluid communication with first opening 26; and housing 14 is configured to open to permit a user to access the chamber. Apparatus 10b also comprises a fluid-permeable sponge applicator 38 that is substantially similar to sponge applicator 38 of FIGS. 1E-1G and 2 (e.g., having a first end 42, a second end 46, and a length 50 extending between the first and second ends 42 and 46, the sponge applicator defining a passage 54 extending through at least a portion of length 50 of sponge applicator 38 and through first end 42, the passage having a substantially circular cross-section). As with apparatus 10, housing 14 of apparatus 10b is configured to removably receive the sponge applicator in the chamber such that the passage is substantially aligned with the first opening of the housing so that a stylus can be passed sequentially through the first opening and the passage such that when passed through the passage the sponge applicator contacts more than half of the cross-sectional perimeter of the stylus.

In the embodiment shown, housing 14 of apparatus 10b: has a second opening 30 through second end 22; passage 54 extends through the first and second ends (42 and 46) of the sponge applicator; and the housing is configured to removably receive the sponge applicator in the chamber such that the passage substantially aligns with the second opening. In some embodiments, the housing does not have opening 30 in second end 22 (has a closed second end) and passage 54 of the sponge applicator does not extend through second end 46 of the sponge applicator (e.g., the passage has a closed end corresponding to the closed end of the housing). Passage 54 of apparatus 10b can have any suitable relaxed inner diameter (e.g., equal to, less than, greater than, or between any of (e.g., about): 0.1, 0.15, 0.2, 0.25, 0.3, 0.35, 0.4, and 0.45 inches). Apparatus 10b can also be configured, as described above, to permit sanitization of styluses having diameters within a functional range.

Apparatus 10b also has several differences from apparatus 10. For example, apparatus 10b is configured to be coupled to a POS device 700. POS device 700 can be nearly any POS device, such as, for example, a POS device configured to process payment cards (e.g., debit, credit, and/or pre-paid cards such as those that have a magnetic stripe) and/or any other devices that include, utilize, or are configured to receive input via, a stylus 704. For example, in the embodiment shown, POS device 700 has a screen 708 configured to receive input via a stylus 704 (e.g., to receive a signature with payment by credit card). More particularly, in the embodiment shown, POS device 700 comprises a stylus slot 712 configured to receive a stylus 704 in a sliding or snapping fashion (e.g., the stylus can be slid and/or snapped into and/or out of stylus slot 712). In the embodiment shown, stylus 704 is coupled to POS device 700 by way of a tether 714 having a length. Tether 714 can comprise any suitable material, such as, for example, wire, string, cord, cable, chain, tape, and/or any other flexible or otherwise configured material that permits the stylus to be moved relative to the POS device to permit a user to use the stylus to provide input to the POS device. Some embodiments do not have a tether 714.

In the embodiment shown, apparatus 10b is configured to be coupled to POS device 700 via a mount or stand 74a. More particularly, stand 74a has an upper portion 78a configured to be coupled, and is shown coupled to, housing 14 (e.g., pivotally coupled or coupled in fixed relation), and stand 74a has a lower portion 82a configured to be coupled to POS device 700 (e.g., via stylus slot 712). In the embodiment shown, lower portion 82a includes a round base portion 716 sized to slide or snap into and/or out of stylus slot 712 (e.g., sized similarly to stylus 704). Lower portion 82a also includes a clip portion 720 configured to extend around a portion of POS device 700 as shown (e.g., to stabilize stand 74a and apparatus 10b such as by preventing stand 74a from rotating relative to POS device 700 such as from rotating beyond limits set by the physical configuration of clip portion 720). In other embodiments, clip portion 720 can be omitted and/or the stand can be configured, modified, and/or omitted in any suitable fashion to permit apparatus 10b to be coupled to a POS device (e.g., POS device 700). For example, the stand can be omitted and apparatus 10b can be coupled to a POS device with adhesive, double-sided tape, screws, and/or the like.

Some embodiments of the present kits comprise a POS device (e.g., POS device 700) and a stylus-sanitization apparatus (e.g., apparatus 10b). In some embodiments, the stylus-sanitization apparatus can be coupled to the POS device. Some embodiments of the present methods comprise: providing a stylus sanitization apparatus (e.g., apparatus 10b); and passing a stylus (e.g., stylus 704) through the passage (e.g., in direction 724 and/or direction 728) of the sponge applicator such that a portion of the sanitization fluid is disposed on the pen. Some embodiments of the present methods comprise: providing a POS device (e.g., POS device 700); providing a stylus (e.g., stylus 704) coupled to the POS device by a flexible tether (e.g., tether 714) having a length; and providing a stylus-sanitization apparatus (e.g., apparatus 10b) within a distance of the POS device that is less than or substantially equal to the length of the tether. Some embodiments of the present kits comprise a housing (e.g., housing 14 of apparatus 10b), and two or more fluid-permeable sponge applicators (e.g., sponge applicator 38).

Figure 11:
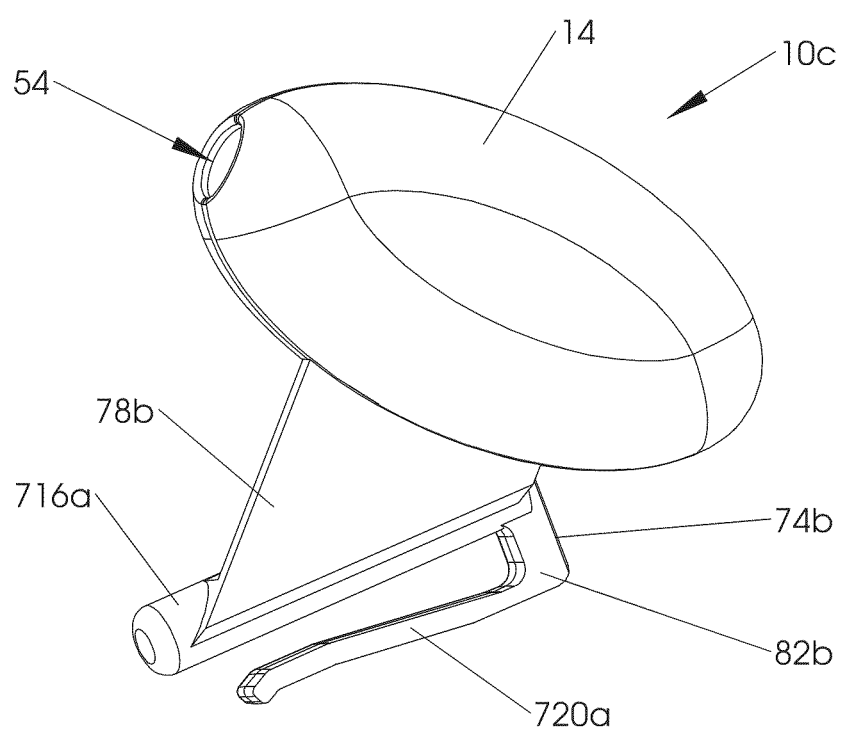
FIG. 11 depicts another embodiment of a stylus-sanitization apparatus.

FIG. 11 depicts another embodiment of a stylus-sanitization apparatus 10c. Apparatus 10c is substantially similar to apparatus 10b of FIGS. 9A-9C and 10. For example, apparatus 10c is also configured to be coupled (e.g., removably coupled) to a point-of-sale (POS) device (e.g., POS device 700 of FIGS. 9A-9C). Apparatus 10c also includes a stand 74b that is similar to stand 74a of apparatus 10b (e.g., that includes an upper portion 78b, and a lower portion 82b with a base portion 716a and clip 720a). In the embodiment shown, stand 74b also includes a base portion 716a configured to be received in a stylus slot (e.g., 712) of a POS device such that housing 14 is supported relative to the POS device. As with apparatus 10b, base portion 716a has a first longitudinal axis, and the passage 54 through the sponge applicator has a second longitudinal axis. However, apparatus 10c is configured such that the first longitudinal axis of base portion 716a is not parallel to the second longitudinal axis of passage 54. For example, in the embodiment shown, the second longitudinal axis (of passage 54) is disposed at an angle of between 30 and 60 degrees (e.g., equal to, greater than, or between any of: 31, 35, 40, 45, 50, 55, and/or 59 degrees) relative to the first longitudinal axis (of base portion 716a). In the embodiment shown, a planar portion 724 extends between housing 14 and base portion 716a, and is laterally offset from the center of base portion 716a. In other embodiments, planar portion 724 can be laterally aligned with (e.g., pass through) the center of base portion 716a.

Figure 12A:
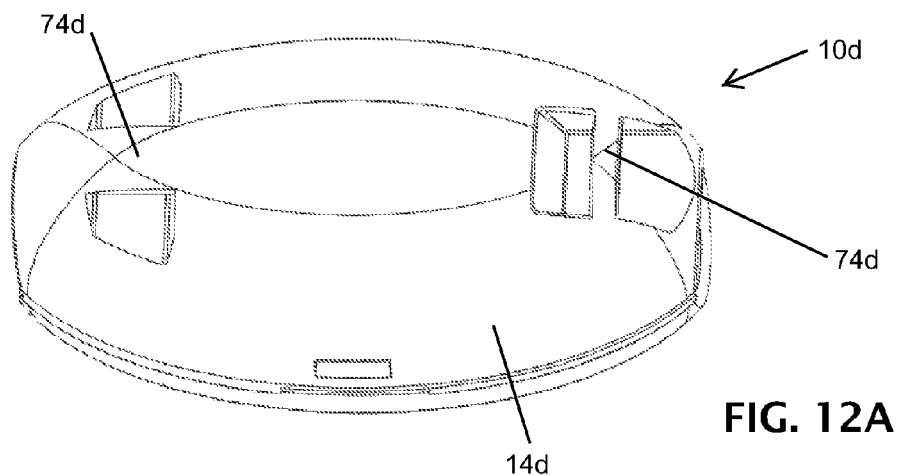
FIGS. 12A-12B depict another embodiment of a pen-sanitization apparatus.
Figure 12B:
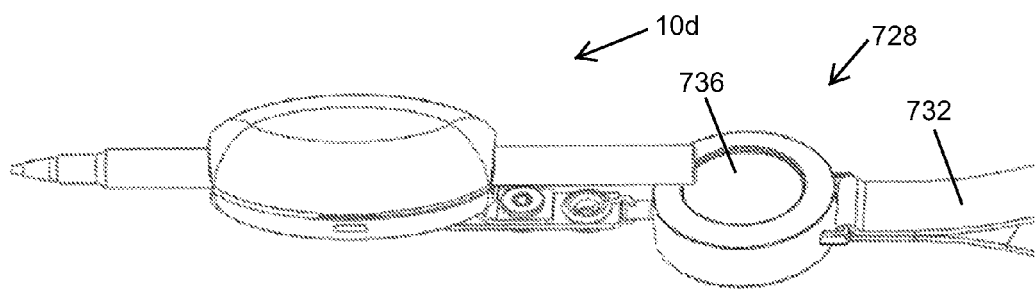

FIGS. 12A-12B depict another embodiment 10d of a pen-sanitization apparatus. Apparatus 10d is substantially similar to apparatus 10, with the primary exception that apparatus 10d does not include stand 74. Instead, apparatus 10d (e.g., housing 14d) includes one or more lanyard loops 74c external to the chamber of the housing. For example, lanyard loops 74d are configured to receive a lanyard 728. In the embodiment shown, apparatus 10d includes two lanyard loops 74d (a vertical lanyard loop that is substantially parallel to the longitudinal axis of passage 54, and a horizontal lanyard loop that is substantially perpendicular to the longitudinal axis of the passage). In the embodiment shown, loops 74d are recessed such that housing defines an opening for each loop that extends inward relative to the outer boundary of housing 14d. In some embodiments, apparatus 10d further comprises a lanyard 728 configured to be coupled to the one or more loops 74d (e.g., one of the loops 74d). In the embodiment shown, lanyard 728 includes a neck portion 732 configured to be looped around the neck of a user, and an extension portion 736 configured to permit a user to retractably extend apparatus 10d from neck portion 732 (e.g., via a spring-loaded spool).

Figure 13A:
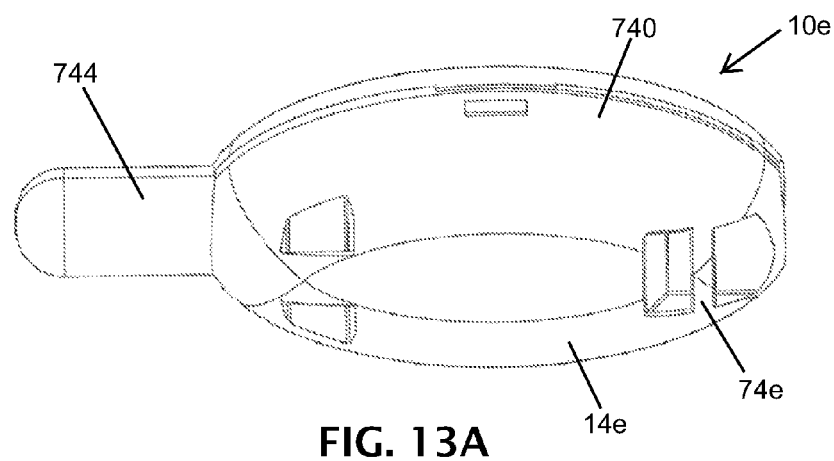
FIGS. 13A-13B depict another embodiment of a pen-sanitization apparatus.
Figure 13B:
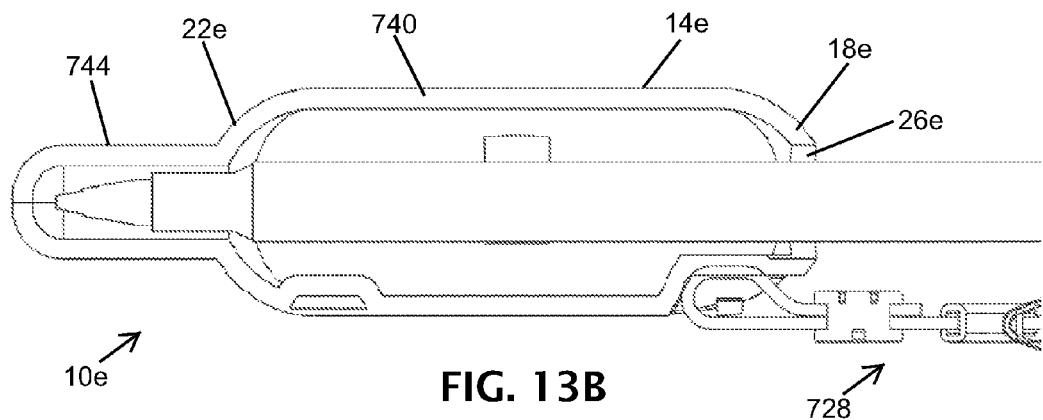

FIGS. 13A-13B depict another embodiment 10e of a pen-sanitization apparatus. Apparatus 10e is similar in many respects to apparatus 10 and to apparatus 10d. For example, apparatus 10e includes lanyard loops 74e and can include a lanyard 728. However, apparatus 10e includes a housing 14e having a body 740 with a first end 18e and a second end 22e.

As shown, housing 14e defines a first opening 26e through the first end, and an elongated tubular portion 744 (e.g., have a closed outer end 748) extending from the second end of the body (e.g., away from the first end of the body). As also shown, body 14e defines a chamber 34e in fluid communication with first opening 26e and tubular portion 744. As with the housings of apparatuses 10 and 10d, housing 10e is configured to open to permit a user to access chamber 34e. In the embodiment shown, housing 14e is configured to removably receive the sponge applicator (not shown) in chamber 34e such that the passage 54 is substantially aligned with first opening 26e and tubular portion 744 of the housing so that a portion of a pen can be passed sequentially through first opening 26e and the passage 30, and into tubular portion 744 (as shown in FIG. 13B) such that when passed through the passage the sponge applicator contacts more than half of the cross-sectional perimeter of the pen. In some embodiments, apparatus 10e is configured such that if a pen is disposed in the housing with a portion of the pen extending into the tubular portion, at least one of the sponge applicator and the tubular portion of the housing will resist removal of the pen from the housing. For example, tubular portion can be provided with one or more internal tabs that will exert an inward pressure on the pen, and/or the passage of the sponge applicator can be provided with a diameter that is less than the diameter of the pen such that the sponge applicator will exert an inward and/or frictional force on the pen.

Figure 14A:
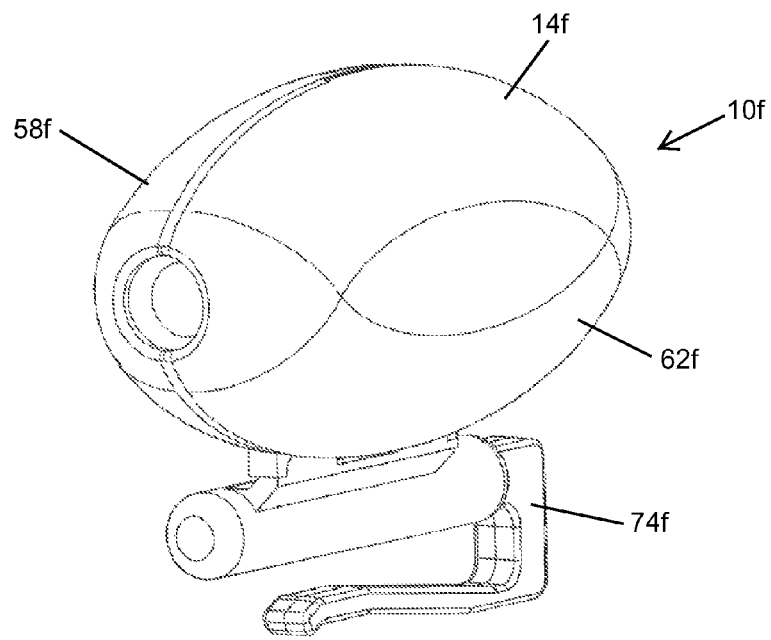
FIGS. 14A-14C depict another embodiment of a pen-sanitization apparatus.
Figure 14B:
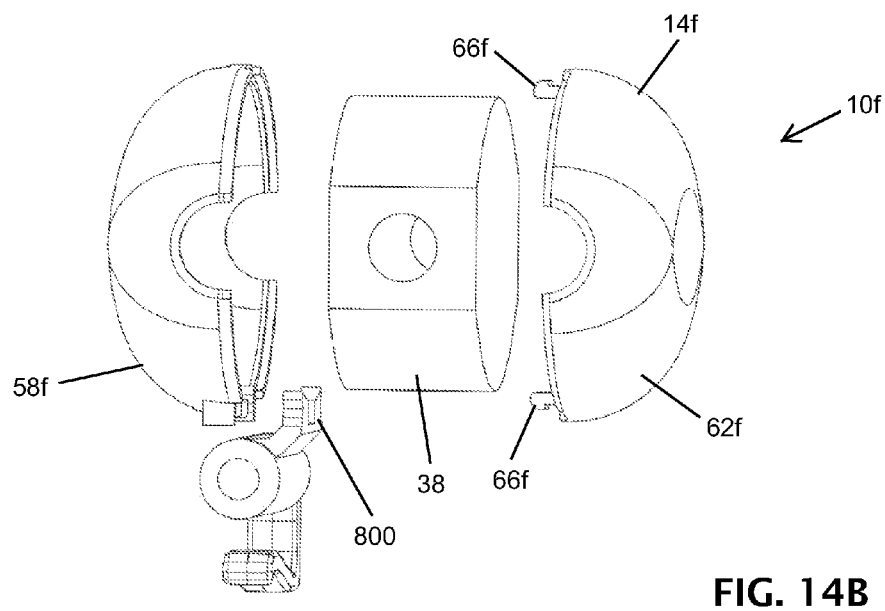
Figure 14C:
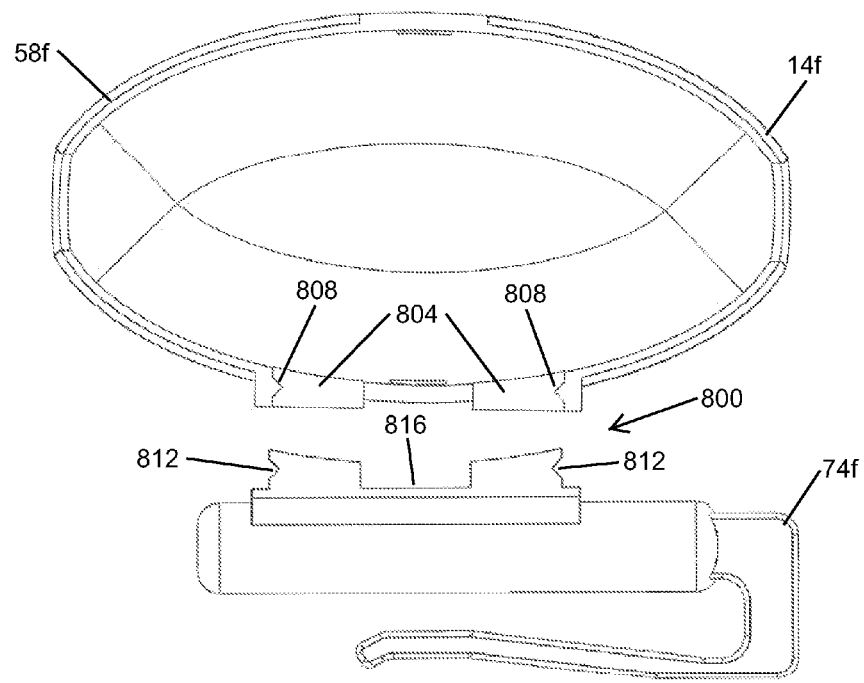

FIGS. 14A-14C depict another embodiment 10f of a pen-sanitization apparatus. In the embodiment shown, housing 14f of apparatus 10f is configured to be removably coupled to a mount 74f. Apparatus 10f is substantially similar to apparatus 10a, with the primary exception that apparatus 10f can be described as having a modular configuration, such that, for example, different mounts (e.g., mount 74f and other mounts similar to the stands and mounts described above) can be interchangably coupled to housing 14f. In the embodiment shown, 14f includes a first (e.g., left) housing member 58f and a second (e.g., right) housing member 62f, and is configured to open by separating a portion (up to all) of left housing member 58f from a portion (up to all) of right housing member 62f. In the embodiment shown, right housing member 62f is configured to be coupled to left housing member 58f (e.g., by way of tabs 66f and corresponding slots 70f (not shown, but similar to slots 70 of apparatus 10)) to define chamber 34f, and to be separated from left housing member 58f to permit a user to access chamber 34f (e.g., to permit access to sponge applicator 38). In other embodiments, left housing member 58f is pivotally coupled to right housing member 62f.

As shown, apparatus 10f is configured to be removably coupled to mount 74f by disposing a portion (attachment portion) 800 of mount 74f between first and second housing members 58f and 62f and closing housing 14f (e.g., by coupling first housing member 58f to second housing member 62f, as shown in FIG. 14A). For example, at least one of first housing member 58f and second housing member 62f defines a notch 804 (e.g., two notches 804, as shown) such that housing 14f is configured to receive attachment portion 800 of the mount between first housing member 58f and second housing member 62f, such that mount 74f is substantially prevented from being removed from the housing unless the housing is at least partially opened (e.g., first and second housing members 58f and 62f are separated at notches 804). In the embodiment shown, housing 14f (e.g., first housing member 58f) includes protrusions 808 extending into notches 804, and attachment portion 800 of mount 74f includes indents 812 corresponding to protrusions 808, such that mounting portion 800 can be pressed or inserted laterally into notches 804 so that protrusions 808 extend into indents 812 to substantially prevent mount 74f from pulling away from first housing member 84b without first laterally separating the mount and the first housing member. In the embodiment shown, attachment portion 800 also includes a notched portion 816 configured to permit the lower one of tabs 66f to extend through or across attachment portion 800 (e.g., such that part of attachment portion 800 is disposed on each side of the lower notch when housing 14 and mount 74f are coupled together).

In the embodiment shown, mount 74b includes a stand configured to be coupled to a point-of-sale device (as described for mounts 74a and 74b described above). In other embodiments, mount 74f can include a stand configured to support the apparatus relative to a surface (e.g., similar to stand 74, described above, but with an attachment portion 800), and/or or a lanyard (e.g., one or more lanyard loops, as described above, but with an attachment portion 800). Some embodiments of the present kits comprise an apparatus 10f with one or more (e.g., two, three, etc.) interchangeable mounts of the same or different types (e.g., a stand configured to support the apparatus relative to a surface, a stand configured to be coupled to a point-of-sale device, and/or a lanyard).

Example

A prototype of apparatus 10, described above, was tested by passing pens dipped in bacterial solution through the apparatus. More particularly, an uncoated sponge applicator 38 was dipped in a solution of 0.26 percent, by weight, of benzalkonium chloride for ten seconds to saturate the sponge applicator with the solution, and the sponge applicator was then installed in housing 14. Additionally, a bacterial solution was produced containing an ambient mix of bacteria obtained from surfaces of food. Three pens of different types, were sequentially dipped into the bacterial solution, and then inserted into the apparatus for periods of 30 seconds, 1 minute, 2 minutes, 5 minutes, and 10 minutes. Each pen was then removed from the apparatus, and dipped and rotated for 3 seconds in a 15 mL centrifuge tubes containing 5 mL of Luria Broth (Sigma-Aldrich Co., USA), a growth medium, to transfer bacteria on the pen to the growth medium; the pen was then removed, and the tube capped to prevent ambient contamination. For a control set, each pen was also dipped in the bacterial solution and rotated in the growth medium immediately after dipping in the bacterial solution (without placement in the apparatus (0 minutes in the apparatus)). All the tubes were put into a shaker and incubated overnight at 37° C. The absorbance of each incubated solution was then measured at 600 nm using a spectrophotometer (Spectrumlab 752S), with a cuvette of non-contaminated Luria Broth as a reference. This particular wavelength is generally regarded as a maximum-absorbance wavelength for an ordinary solution of bacteria. The absorbance measured from each incubated solution is listed in Table 1 below. The absorbance was between 0.331 and 0.776 for the growth media directly exposed to the non-sanitized pens (that were not placed in the apparatus (0 minutes)), and indicate the presence of bacteria on the pens. Sanitization of the pens in the apparatus for any of the tested time periods resulted in nominal absorbance readings that are believed to be within the variability of a zero reading of the spectrophotometer, meaning that essentially or almost no bacteria were detected in the growth medium after a pen was sanitized in the apparatus for 30 or more seconds.

TABLE 1

| | Absorbance measured at 600 nm of Incubated Solutions (0.26% BZK) | | |
|---|---|---|---|
| Time in Apparatus (minutes) | Pen No. 1 | Pen No. 2 | Pen No. 3 |
| 0 | 0.331 | 0.776 | 0.487 |
| 0.5 | 0.001 | 0.002 | 0.002 |
| 1 | 0.000 | 0.000 | 0.001 |
| 2 | 0.004 | 0.001 | 0.002 |
| 5 | 0.003 | 0.003 | 0.002 |
| 10 | 0.000 | 0.002 | 0.000 |

A second test was also performed that was identical in process to the first test, except that a 0.13 percent by weight solution of benzalkonium chloride was used. The absorbance measured from each incubated solution is listed in Table 2. The absorbance was between 1.284 and 1.629 for the growth media directly exposed to the non-sanitized pens (that were not placed in the apparatus (0 minutes)), and indicate the presence of bacteria on the pens. Sanitization of the pens in the apparatus for any of the tested time periods resulted in nominal absorbance readings between that are believed to be within the variability of a zero reading of the spectrophotometer, meaning that essentially or almost no bacteria were detected in the growth medium after a pen was sanitized in the apparatus for 30 or more seconds.

TABLE 2

| | Absorbance measured at 600 nm of Incubated Solutions (0.13% BZK) | | |
|---|---|---|---|
| Time in Apparatus (minutes) | Pen No. 1 | Pen No. 2 | Pen No. 3 |
| 0 | 1.629 | 1.284 | 1.467 |
| 0.5 | 0.000 | 0.000 | 0.002 |
| 1 | 0.001 | 0.002 | 0.001 |
| 2 | −0.001 | 0.001 | 0.001 |
| 5 | −0.001 | 0.000 | −0.001 |
| 10 | 0.000 | 0.000 | 0.001 |

Any of the present apparatuses (e.g., 10, 100, 200, 10*a*, 200*a*, 10*b*), kits, and/or methods can be configured to have any of the features described and/or depicted for any of the other apparatuses (e.g., 10, 100, 200, 10*a*, 200*a*, 10*b*), kits, and/or methods. For example, the first end and/or second end of the sponge applicator of any of the apparatuses can be configured to be fluid-impermeable.

The various illustrative embodiments of apparatuses, kits, and methods described herein are not intended to be limited to the particular forms disclosed. Rather, they include all modifications, equivalents, and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A pen-sanitization apparatus comprising:
    a housing having a first end and a second end, the housing defining a first opening through the first end, a second opening through the second end, and a chamber in fluid communication with the first and second openings, the housing configured to open to permit a user to access the chamber; and
    a fluid-permeable sponge applicator having a first end, a second end, and a length extending between the first and second ends, the sponge applicator defining a passage extending through the sponge applicator and through the first and second ends of the sponge applicator, the passage having a substantially circular cross-section; and
    a stand having a first end configured to be pivotally coupled to the housing and a second end configured to be coupled to a surface such that the stand supports the apparatus;
    where the housing is configured to removably receive the sponge applicator in the chamber such that the passage is substantially aligned with the first and second openings of the housing so that a pen can be passed sequentially through the first opening, the passage, and the second opening such that when passed through the passage the sponge applicator contacts more than half of the cross-sectional perimeter of the pen.

2. The sanitization apparatus of claim 1, where the sponge applicator encircles the entire length of the passage, and where the apparatus is configured such that pens having various diameters within a functional range can be passed sequentially through the first opening, passage, and second opening such that when passed through the passage the sponge applicator contacts more than half of the cross-sectional perimeter of the pen.

3. The sanitization apparatus of claim 1, where the first and second ends of the sponge applicator are configured to be fluid-impermeable.

4. The sanitization apparatus of claim 3, where an outer surface of the sponge applicator between the first and second ends of the sponge applicator are coated with a fluid impermeable material.

5. The sanitization apparatus of claim 1, where the housing is configured to be removably coupled to a mount.

6. The sanitization apparatus of claim 5, where the housing comprise a first housing member and a second housing member, and is configured to be opened by separating a portion of the first housing member from a portion of the second housing member, and is configured to be removably coupled to a mount by disposing a portion of the mount between the first and second housing members and closing the housing.

7. The sanitization apparatus of claim 5, where the mount includes at least one of: a stand configured to support the apparatus relative to a surface, a stand configured to be coupled to a point-of-sale device, or a lanyard.

8. The sanitization apparatus of claim 1, where the housing comprises a first housing member and a second housing member, and is configured to open by separating a portion of the first housing member from a portion of the second housing member along a longitudinal boundary intersecting the first opening.

9. The sanitization apparatus of claim 8, where the first housing member is configured to be coupled to the second housing member to define the chamber and configured to be separated from the second housing member to permit a user to access the chamber.

10. The sanitization apparatus of claim 1, further comprising:
    a liquid crystal display (LCD) screen.

11. The sanitization apparatus of claim 1, further comprising:
    a sanitization fluid absorbed in the sponge applicator.

12. The sanitization apparatus of claim 11, where the sanitization fluid comprises one or more ingredients selected from the group consisting of: alcohols, ethanol, isopropanol, aldehydes, oxidizing agents, acids, phenolics, ammoniums, and chlorine.

13. The sanitization apparatus of claim 11, where the apparatus is configured such that if the sponge applicator is disposed in the chamber and a pen is passed sequentially through the first opening, the passage, and the second opening, the sanitization fluid is applied to the pen by the sponge applicator without any external pumping mechanism.

14. The sanitization apparatus of claim 1, where the first and second openings of the housing are each circular and have a diameter that is larger than a relaxed inner diameter of the passage through the sponge applicator.

15. A sanitization kit comprising:
- a housing having a first end and a second end, the housing defining a first opening through the first end, a second opening through the second end, and a chamber in fluid communication with the first and second openings, the housing configured to open to permit a user to access the chamber;
- a stand having a first end configured to be pivotally coupled to the housing and a second end configured to be coupled to a surface such that the stand supports the apparatus; and
- two or more fluid-permeable sponge applicators each having a first end, a second end, and a length extending between the first and second ends, the sponge applicator defining a passage extending through the sponge applicator and through the first and second ends of the sponge applicator;
- where the housing is configured to removably receive the sponge applicator in the chamber such that the passage is substantially aligned with the first and second openings of the housing so that a pen can be passed sequentially through the first opening, the passage, and the second opening such that when passed through the passage the sponge applicator contacts more than half of the cross-sectional perimeter of the pen; and
- where the housing is configured to removably and interchangeably receive each of the two or more sponge applicators individually.

* * * * *